US010757228B1

(12) United States Patent
Bhimavarapu et al.

(10) Patent No.: US 10,757,228 B1
(45) Date of Patent: Aug. 25, 2020

(54) PATIENT CARE DEVICES WITH ON-BOARD NETWORK COMMUNICATION

(71) Applicant: Stryker Corporation, Kalamazoo, MI (US)

(72) Inventors: Krishna Sandeep Bhimavarapu, Kalamazoo, MI (US); Janani Gopalkrishnan, Portage, MI (US); Jason A. Vanderplas, Kalamazoo, MI (US); Michael Joseph Hayes, Kalamazoo, MI (US); Marco Constant, Portage, MI (US); Eileen Siew Chin Cheong Youne, Houston, TX (US)

(73) Assignee: Stryker Corporation, Kalamazoo, MI (US)

( * ) Notice: Subject to any disclaimer, the term of this patent is extended or adjusted under 35 U.S.C. 154(b) by 59 days.

(21) Appl. No.: 15/903,477

(22) Filed: Feb. 23, 2018

Related U.S. Application Data

(60) Provisional application No. 62/464,565, filed on Feb. 28, 2017.

(51) Int. Cl.
*H04L 29/06* (2006.01)
*G16H 40/63* (2018.01)
(Continued)

(52) U.S. Cl.
CPC .............. *H04L 69/08* (2013.01); *A61G 7/05* (2013.01); *G16H 40/63* (2018.01); *H04L 29/0653* (2013.01); *H04L 67/12* (2013.01)

(58) Field of Classification Search
CPC ...... H04L 69/08; H04L 29/0653; H04L 67/12; G16H 40/63; A61G 7/05
See application file for complete search history.

(56) References Cited

U.S. PATENT DOCUMENTS 6,453,297 B1 * 9/2002 Burks .................. G06Q 40/02
705/3
7,319,386 B2 1/2008 Collins, Jr. et al.
(Continued)

OTHER PUBLICATIONS

InTouch Critical Care Bed, Ref Model FL27 (2131/2141), Version 2.5, Stryker Operations Manual, Apr. 2012.
(Continued)

*Primary Examiner* — Mohamed A. Wasel
(74) *Attorney, Agent, or Firm* — Warner Norcross + Judd LLP

(57) ABSTRACT

Patient care devices, such as person support apparatuses and thermal control units, include multiple internal network nodes. A controller is associated with each node and at least one of the controllers is adapted to process a message received from another node, convert the message from a first communication protocol to a different communication protocol, and forward the message to yet another node using the different communication protocol. One or more of the controllers may also or alternatively reformulate a packet received in a first format from a first node and forward the reformulated packet to another node. One or more controllers may also send messages over a common data link layer wherein some of the messages are formatted according to different message protocols. Some controllers may utilize real time operating systems while others may not.

21 Claims, 7 Drawing Sheets

(51) Int. Cl.
*A61G 7/05* (2006.01)
*H04L 29/08* (2006.01)

(56) References Cited

U.S. PATENT DOCUMENTS

| | | | |
|---|---|---|---|
| 7,430,608 B2 | 9/2008 | Noonan et al. | |
| 7,746,218 B2 | 6/2010 | Collins, Jr. et al. | |
| 7,840,694 B2 | 11/2010 | Yamaki | |
| 8,082,160 B2 | 12/2011 | Collins, Jr. et al. | |
| 8,120,471 B2 | 2/2012 | Collins, Jr. et al. | |
| 8,121,856 B2 | 2/2012 | Huster et al. | |
| 8,312,174 B2 | 11/2012 | Espina Perez et al. | |
| 8,421,606 B2 | 4/2013 | Collins, Jr. et al. | |
| 8,536,990 B2 | 9/2013 | Collins, Jr. et al. | |
| 8,618,918 B2 | 12/2013 | Tallent et al. | |
| 8,756,078 B2 * | 6/2014 | Collins, Jr. | G06F 19/3418 705/3 |
| 8,917,166 B2 | 12/2014 | Collins, Jr. et al. | |
| 9,081,696 B2 | 7/2015 | Smith | |
| 9,253,259 B2 | 2/2016 | Tallent et al. | |
| 9,466,877 B2 | 10/2016 | Dixon et al. | |
| 9,517,034 B2 | 12/2016 | Collins, Jr. et al. | |
| 9,569,591 B2 * | 2/2017 | Vanderpohl, III | A61G 7/012 |
| 9,966,997 B2 * | 5/2018 | Hayes | H04B 5/0037 |
| 10,004,654 B2 * | 6/2018 | Zerhusen | A61G 7/1017 |
| 10,034,979 B2 * | 7/2018 | Bechtel | G16H 70/00 |
| 10,290,071 B2 * | 5/2019 | Heil | G16H 40/63 |
| 10,360,787 B2 * | 7/2019 | Embree | G16H 40/63 |
| 2009/0112630 A1 * | 4/2009 | Collins, Jr. | H04L 67/12 705/3 |
| 2009/0193435 A1 | 7/2009 | Yamaki | |
| 2012/0316892 A1 | 12/2012 | Huster et al. | |
| 2012/0331082 A1 * | 12/2012 | Smith | H04L 49/351 709/208 |
| 2013/0283529 A1 | 10/2013 | Hayes et al. | |
| 2014/0080413 A1 | 3/2014 | Hayes et al. | |
| 2015/0231006 A1 | 8/2015 | Bhimavarapu et al. | |
| 2015/0290060 A9 | 10/2015 | Hayes et al. | |
| 2016/0038361 A1 | 2/2016 | Bhimavarapu et al. | |
| 2016/0283665 A1 | 9/2016 | Sampath et al. | |
| 2016/0358452 A1 | 12/2016 | Dixon et al. | |
| 2017/0004106 A1 | 1/2017 | Joshua et al. | |
| 2017/0035295 A1 | 2/2017 | Collins, Jr. et al. | |

OTHER PUBLICATIONS

InTouch Critical Care Bed, Model FL27 (2131/2141), Version 2.4, Stryker Maintenance Manual, Jun. 2010.

Steve Corrigan, Introduction to the Controller Area Network (CAN), Application Report, Texas Instruments, Jul. 2008.

* cited by examiner

US 10,757,228 B1

PATIENT CARE DEVICES WITH ON-BOARD NETWORK COMMUNICATION

CROSS-REFERENCE TO RELATED APPLICATIONS

This application claims priority to U.S. provisional patent application Ser. No. 62/464,565 filed Feb. 28, 2017, by inventors Krishna S. Bhimavarapu et al. and entitled PATIENT CARE DEVICES WITH ON-BOARD NETWORK COMMUNICATION, the complete disclosure of which is incorporated herein by reference.

BACKGROUND

The present disclosure relates to patient care devices, such as person support apparatuses (e.g. beds, stretchers, chairs, recliners, operating tables, cots, etc.), thermal control units adapted to control a person's temperature, and other types of medical devices.

Some patient care devices include embedded systems having multiple nodes that communicate with each other. The nodes typically communicate with each other using the same medium and same protocols. Redesigns and/or modifications to the patient care devices that involve using a different communication medium or protocol are often difficult.

SUMMARY

Patient care devices according to one or more aspects of the present disclosure include embedded communication systems that provide greater flexibility for changes and redesigns. The embedded communication systems allow different types of communication protocols and/or communication media to be used, thereby allowing the embedded nodes to communicate using media and/or protocols that are better suited to the particular communication needs of the different nodes. In some instances, different data link layer protocols (layer 2) of the Open System Interconnection (OSI) model are used between different nodes. Different physical layers may also be used between different nodes. Messages formatted in different network layers (or higher layers) may be transmitted over the various communication media and may be reformulated using different lower network layers (i.e. data link and physical layers) as the messages are passed from node to node. In some instances, different operating systems and/or different types of operating systems (e.g. real time versus non-real time) are used in several of the nodes.

According to a first embodiment of the present disclosure, a person support apparatus is provided that includes a support surface; first, second, and third nodes; first and second communication media, and a controller associated with the second node. The support surface is adapted to support a person. The first, second, and third nodes are adapted to perform first, second, and third functions, respectively, associated with the person support apparatus. The first communication medium is coupled between the first and second nodes. The second communication medium is coupled between the second and third nodes. The controller processes a message received via the first communication medium and sent from the first node using a first communication protocol, converts the message from the first communication protocol to a second communication protocol, and forwards the message over the second communication medium using the second communication protocol.

According to other aspects, the first communication protocol is an Ethernet communication protocol and the second communication protocol is a non-Ethernet protocol.

In some embodiments, one of the first and second communication media conforms to the RS-485 standard of the Telecommunications Industry Association and Electronic Industries Alliance (TIA/EIA) and the other of the first and second communication media conforms to the Controller Area Network (CAN) 11898-2 standard of the International Organization for Standardization (ISO).

In still other embodiments, both the first and second communication protocols are selected from the following group: a Controller Area Network (CAN) protocol (ISO 11898-1), an RS-485 protocol, an $I^2C$ protocol, an Ethernet protocol (IEEE 802.3), and a Serial Peripheral Interface (SPI) protocol.

In some embodiments, the message travels over the first communication medium as a first packet having a first payload and a first header, and the message is forwarded over the second communication medium as a second packet having a second payload and a second header. In some instances, the controller moves at least some data contained within the first header into the second payload. In other instances, the controller moves at least some data contained within the first payload into the second header. Still further, in some instances, the controller may move the entire first header and first payload into the second payload.

According to still other aspects, the first payload of the first packet includes a first identifier identifying a final destination of the message and the controller is adapted to insert the first identifier into the second header of the second packet.

Some patient care devices may further include a fourth node coupled to the third node via a third communication medium. When so included, the third node includes a second controller adapted to process the message received via the second communication medium and sent from the second node using the first second protocol, convert the message from the second communication protocol to a third communication protocol, and forward the message over the third communication medium using the third communication protocol.

The nodes may each include a microcontroller, and in some embodiments, a first one of the microcontrollers uses a first operating system and a second one of the microcontrollers uses a second operating system. At least one of the operating systems is a real-time operating system and at least one of the operating systems is not a real-time operating system. The real time operating system is used, in some instances, to control at least one motor on the person support apparatus.

According to another embodiment of the present disclosure, a person support apparatus is provided that includes a support surface, a node, a first communication medium, a second communication medium, and a controller associated with the node. The support surface is adapted to support a person thereon. The node performs a function associated with the person support apparatus. The first and second communication media are coupled to the node. The controller reformulates a packet received in a first format or protocol via the first communication medium into a second format or protocol, and forwards the reformulated packet over the second communication medium.

According to other embodiments, the packet includes a header and a payload and the reformulated packet includes a reformulated header and a reformulated payload. The reformulated header may include at least some data from the payload of the packet and/or the reformulated payload may include at least some data from the header of the packet.

In some embodiments, the reformulated packet includes a first reformulated packet containing a first portion of the data contained within the packet and a second reformulated packet containing a second portion of the data contained within the packet. The controller transmits both the first and second reformulated packets over the second communication medium.

According to another embodiment of the present disclosure, a person support apparatus is provided that includes a support surface, first and second nodes, a communication medium, and a controller associated with the first node. The support surface is adapted to support a person thereon. The first and second nodes are adapted to perform first and second functions associated with the person support apparatus. The communication medium is coupled between the first and second nodes. The controller sends first and second messages over the communication medium to the second node using a first data link layer protocol. The first message is defined according to a first message protocol and the second message is defined according to a second message protocol.

According to other aspects, the first message protocol is a publicly available protocol and the second message protocol is a confidential proprietary protocol.

The first data link layer defines a packet structure having a header and a payload, and the controller is adapted in some embodiments to insert the entire first message into the payload of a first packet and to insert only a portion of the second message into the payload of a second packet.

The first data link layer is defined in accordance with the Controller Area Network (CAN) 11898-1 standard of the Organization for Standardization (ISO) and/or in accordance with at least one of the 802.3 standards of the Institute of Electrical and Electronics Engineers (IEEE), in some embodiments.

In some instances, one of the message protocols is an Internet Protocol (IPv4 and/or IPv6) and/or a message protocol defined in accordance with specification 301 of the CAN in Automation (CiA) organization (CANopen). One of the message protocols may also or alternatively be a proprietary protocol.

According to another embodiment of the present disclosure, a person support apparatus is provided that includes a support surface, first and second nodes, a first communication medium, and first and second controllers. The first and second nodes are adapted to perform first and second functions, respectively, associated with the person support apparatus. The first communication medium is coupled between the first and second nodes. The first controller is associated with the first node and is adapted to execute a first operating system. The second controller is associated with the second node and is adapted to execute a second operating system different from the first operating system.

According to other aspects, the first operating system is a hard real-time operating system (RTOS) and the second operating system is not an RTOS.

In some embodiments, the first controller is adapted to send first and second messages over the communication medium to the second node using a first data link layer protocol. The first message is defined according to a first message protocol and the second message is defined according to a second message protocol.

The second controller, in some embodiments, reformulates a packet received in a first format via the first communication medium into a second format. The second controller forwards the reformulated packet over the second communication medium in the second format.

In any of the embodiments disclosed herein, the person support apparatus further include one or more of the following: a plurality of lifts adapted to change a height of the support surface; a plurality of siderails movable between raised and lowered positions; and a plurality of wheels adapted to support the person support apparatus.

Before the embodiments of the disclosure are explained in detail, it is to be understood that the disclosure is not limited to the details of operation or to the details of construction and the arrangement of the components set forth in the following description or illustrated in the drawings. The disclosure may be implemented in various other embodiments and is capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the disclosure to any specific order or number of components. Nor should the use of enumeration be construed as excluding from the scope of the disclosure any additional steps or components that might be combined with or into the enumerated steps or components.

DETAILED DESCRIPTION OF THE EMBODIMENTS

Figure 1:
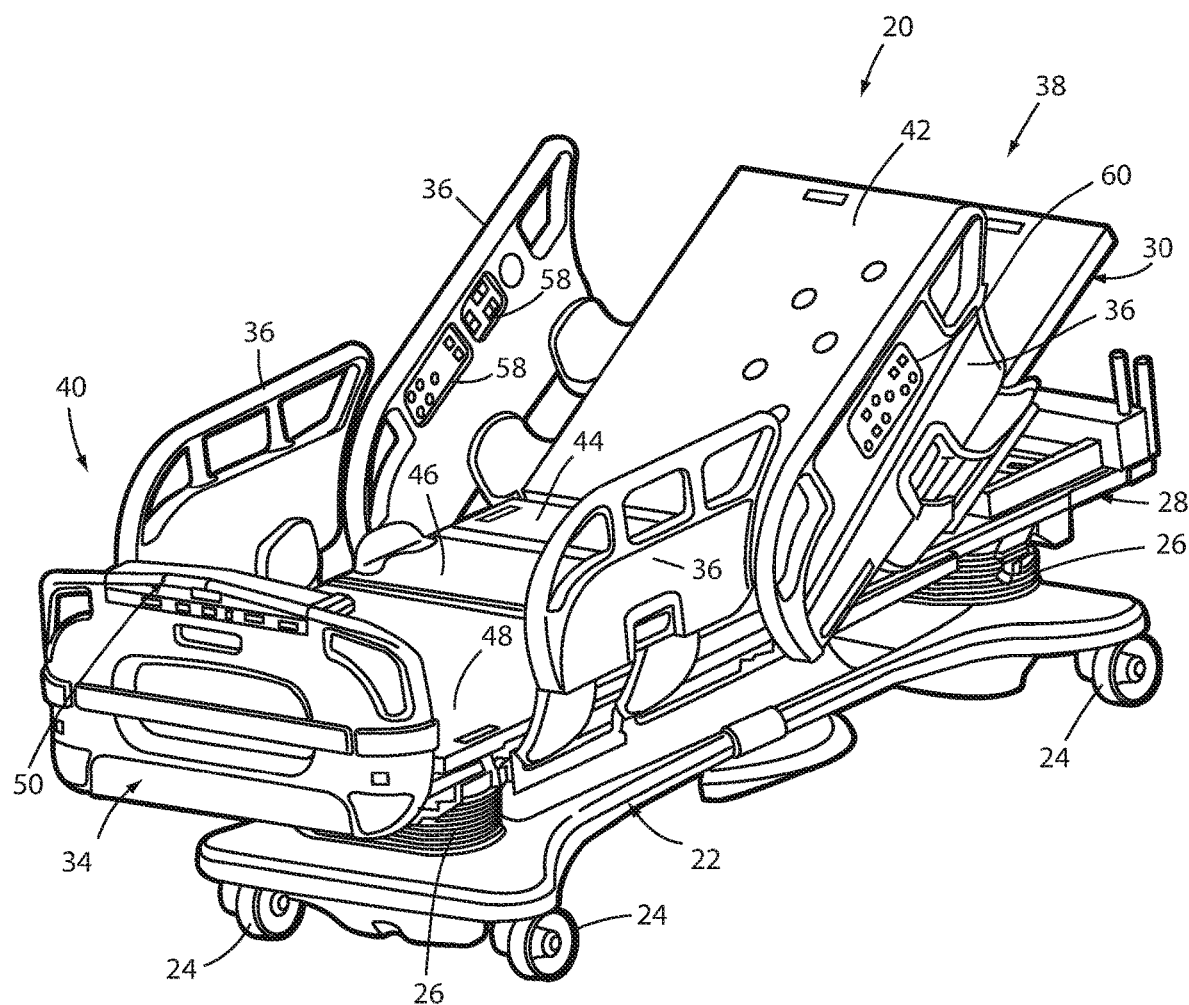
FIG. 1 is a perspective view of one example of a person support apparatus according to one embodiment of the present disclosure.

FIG. 1 illustrates a person support apparatus 20 that includes an improved communications and control system according to one embodiment. Although the particular form of person support apparatus 20 illustrated in FIG. 1 is a bed adapted for use in a hospital or other medical setting, it will be understood that person support apparatus 20 could, in different embodiments, be a cot, a stretcher, a gurney, a recliner, an operating table, a residential bed, or any other structure capable of supporting a person, whether stationary or mobile and/or whether medical or residential. Still other forms of person support apparatuses can be used.

In general, person support apparatus 20 includes a base 22 having a plurality of wheels 24, a pair of lifts 26 supported on the base, a litter frame 28 supported on the lifts 26, and a support deck 30 supported on the litter frame 28. Person support apparatus 20 further includes a headboard (not shown), a footboard 34, and a plurality of siderails 36. Siderails 36 are all shown in a raised position in FIG. 1 but are each individually movable to a lower position in which ingress into, and egress out of, person support apparatus 20 is not obstructed by the lowered siderails 36.

Lifts 26 are adapted to raise and lower litter frame 28 with respect to base 22. Lifts 26 may be hydraulic actuators, electric actuators, pneumatic actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 38 and a foot end 40, each of whose height can be independently adjusted by the nearest lift 26. Person support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard, footboard 34, and siderails 36. Support deck 30 provides a support surface for a mattress (not shown in FIG. 1), or other soft cushion, so that a person may lie and/or sit thereon. The top surface of the mattress or other cushion forms a support surface for the occupant. Support deck 30 is made of a plurality of sections, some of which are pivotable about generally horizontal pivot axes. In the embodiment shown in FIG. 1, support deck 30 includes a head section 42, a seat section 44, a thigh section 46, and a foot section 48. Head section 42, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

Litter frame 28 is supported by two lift header assemblies (not shown) positioned on top of lifts 26. Each lift header assembly includes a pair of force sensors, which may be load cells, or other types of force sensors, such as, but not limited to, linear variable displacement transducers and/or any one or more capacitive, inductive, and/or resistive transducers that are configured to produce a changing output in response to changes in the force exerted against them. The force sensors are adapted to detect the weight of not only those components of person support apparatus 20 that are supported by litter frame 28 (including litter frame 28 itself), but also any objects or persons who are wholly or partially being supported by support deck 30. As will be discussed in greater detail below, these force sensors may be part of an exit detection system and/or a scale system of person support apparatus 20.

The mechanical construction of person support apparatus 20 may be the same as or similar to the mechanical construction of the Model 3002 S3 bed manufactured and sold by Stryker Corporation of Kalamazoo, Mich. This mechanical construction is described in greater detail in the Stryker Maintenance Manual for the MedSurg Bed, Model 3002 S3, published in 2010 by Stryker Corporation of Kalamazoo, Mich., the complete disclosure of which is incorporated herein by reference. It will be understood by those skilled in the art that person support apparatus 20 can be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of person support apparatus 20 may also take on forms different from what is disclosed in the aforementioned references.

Person support apparatuses 20 may also or alternatively be implemented as stretchers, cots, recliners, non-reclining chairs, operating tables, or in other manners. When implemented as a stretcher or cot, person support apparatuses 20 may be constructed in any of the manners disclosed in commonly assigned U.S. Pat. No. 8,051,511 issued to Nahavandi et al. on Nov. 8, 2011 and entitled EMERGENCY STRETCHER; or commonly assigned U.S. Pat. No. 5,537,700 issued to Way et al. on Jul. 23, 1996 and entitled EMERGENCY STRETCHER WITH X-FRAME SUPPORT, the complete disclosures of both of which are hereby incorporated by reference herein. When person support apparatus 20 is implemented as a recliner, it may be constructed in any of the manners disclosed in commonly assigned U.S. patent application Ser. No. 14/212,253 filed Mar. 14, 2014 by inventors Christopher Hough et al. and entitled MEDICAL SUPPORT APPARATUS, the complete disclosure of which is also incorporated herein by reference. Still other constructions of person support apparatuses 20 may be used when one or more of the person support apparatuses 20 are implemented as cots, stretchers, and/or recliners.

Person support apparatus 20 further includes a user interface 50 that enables a user of person support apparatus 20 to control one or more aspects of person support apparatus 20. User interface 50 is implemented in the embodiment shown in FIG. 1 as a control panel having a lid (flipped down in FIG. 1) underneath which is positioned a plurality of controls. The controls may be implemented as buttons, dials, switches, or other devices. User interface 50 may also include a display for displaying information regarding person support apparatus 20. The display is a touchscreen in some embodiments. Although FIG. 1 illustrates user interface 50 mounted to footboard 34, it will be understood that user interface 50 can be positioned elsewhere.

Person support apparatus 20 also includes a pair of occupant user interfaces 58 and a pair of caregiver user interfaces 60 (FIG. 1). Occupant user interfaces 58 are positioned on an inside surface of one or both of the head end siderails 36. Caregiver user interfaces 60 are positioned on an outside surface of one or both of the head end siderails 36. Occupant user interfaces 58 include controls intended to be used by an occupant, such as, but not limited to, the up/down movement of litter frame 28, the pivoting of various of the deck sections, the contacting of—and communication with—a remotely positioned nurse, and the control of one or more environmental features (e.g. volume and/or channel of a nearby television, etc.). Caregiver user interfaces 60 include controls intended to be used by a caregiver associated with the occupant of person support apparatus 20, such as, but not limited to, a brake of person support apparatus 20, the exit detection subsystem incorporated into person support apparatus 20, and/or one or more lockouts that lock out selected controls of occupant user interfaces 58.

Figure 2:
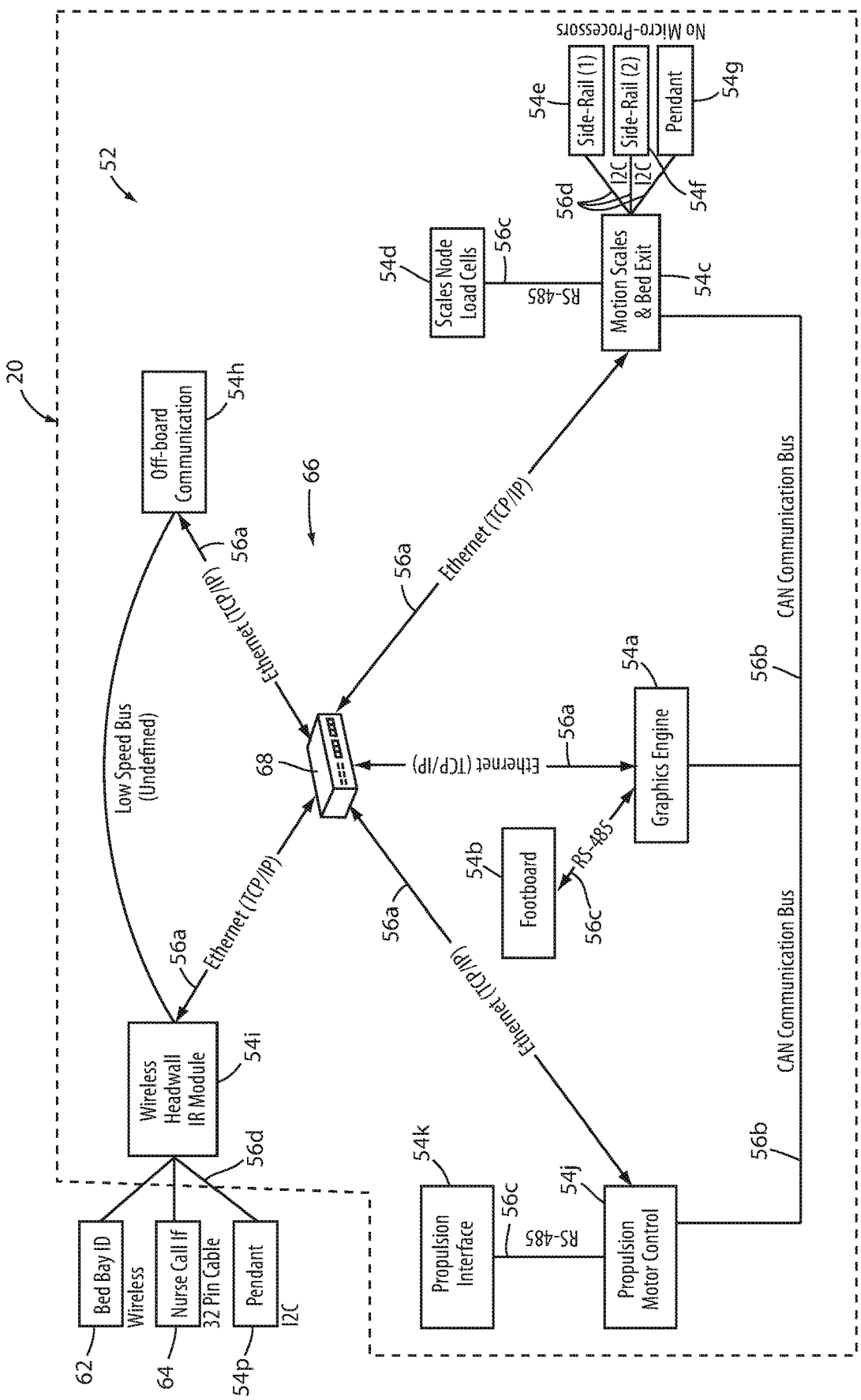
FIG. 2 is a block diagram of an illustrative control system incorporated into the person support apparatus of FIG. 1.

FIG. 2 illustrates one example of a control system 52 for person support apparatus 20. Control system 52 includes a plurality of nodes 54. Each of the nodes 54 is coupled to one or more other nodes by a communication medium 56. Each of the nodes performs specific functions that are described in more detail below. As will also be described in greater detail below, nodes 54 include electronic circuit boards that assist in one or more of the following: controlling the motion of various devices (pumps, motors and actuators); displaying information from the various devices or neighboring devices; providing user interfaces for input by users; measuring weights with an on-board scale system; communicating with a healthcare facility's network including its nurse call system; driving a device within the hospital environment by use of a manual user input, such as drive handles, or by receiving input via one or more load cells or strain gages; receiving feedback or other sensor information from various devices using sensors; and receiving and transmitting data both onboard person support apparatus 20 and off-board person support apparatus 20.

Although FIG. 2 illustrates a specific architecture of control system 52 having a specific number of nodes 54 connected together in a specific way by various communication media 56, it will be understood that this particular architecture is only illustrative, and that control system 52 can be varied in terms of the number of nodes 54, their function, their connections to each other, and/or the communication media 56 used to couple the nodes 54 together.

In the embodiment shown in FIG. 2, nodes 54 include a graphics engine node 54a, a footboard node 54b, a motion control node 54c, a scale node 54d, a first siderail node 54e, a second siderail node 54f, a wired pendant node 54g, an off-board communication node 54h, a headwall node 54i, a propulsion motor control node 54j, a propulsion interface node 54k, and a wireless pendant node 54p. With the exception of nodes 54e, 54f, and 54g, each of the nodes includes a controller, such as, but not limited to, a conventional microcontroller. One or more transceivers are also included in each node, as will be described more below. The functions carried out by each of these nodes will now be described.

Graphics engine node 54a controls the graphics that are displayed on one or more displays of person support apparatus 20. At least one such display is incorporated into footboard 34 and may be positioned adjacent, or integrated into, user interface 50. One or more additional displays may also be included, such as one or more displays mounted to siderails 36. In other embodiments, the display of footboard 34 is moved to a different location on person support apparatus 20. In any of the embodiments disclosed herein, the display may be configured to function only as a display, or it may be configured as a touchscreen display that is sensitive to user touch.

Graphics engine node 54a includes memory for storing the graphics that are displayed on the one or more displays, as well as programming instructions for carrying out the display of those graphics. In some embodiments, graphics engine node 54a delivers graphics to the display that are organized in a scalable vector graphics (SVG) format. In other embodiments, graphics engine node 54a delivers graphics using another format.

Footboard node 54b oversees and controls user interface 50 of footboard 34. User interface 50, in at least some embodiments, includes a plurality of buttons for activating and deactivating motors used to move various components of person support apparatus 20. In addition to controlling movement of person support apparatus 20, user interface 50 also allows a user to take weight measurements of a person supported on support apparatus 20, configure alert settings, and control other aspects of person support apparatus 20. Footboard node 54b controls the communication between nodes 54 necessary to carry out the control of the motors, take weight readings, and configure alerts.

In some embodiments, a powered mattress is added to person support apparatus 20 that is controllable via user interface 50. In those embodiments, footboard node 54b is in communication with the one or more buttons, or other controls, that are used to control aspects of the mattress. To carry out this control, footboard node 54b sends messages to the mattress over one or more of the communication media 56, as will be discussed more below. These messages inform the mattress of which buttons and/or controls have been activated or deactivated by the user. In the configuration of control system 52 shown in FIG. 2, such messages pass from footboard node 54b to graphics engine node 54a to off-board communication node 54h. Off-board communication node 54h is communicatively coupled to the mattress, either via a cable (e.g. a USB cable) or via a wireless connection. One example of such a wireless connection to the mattress is disclosed in commonly assigned U.S. Pat. No. 9,289,336 issued Mar. 22, 2016, to inventors Clifford Lambarth et al. and entitled PATIENT SUPPORT WITH ENERGY TRANSFER, the complete disclosure of which is incorporated herein by reference. Other types of wireless communication with the mattress may also be carried out.

Motion control node 54c controls the movement of person support apparatus 20. Motion control node 54c therefore communicates directly with the motors incorporated into person support apparatus 20. The motors carry out movement of various components of person support apparatus 20, such as, but not limited to, the up/down movement of litter frame 28 whose height is adjustable with respect to base 22 by way lifts 26. Motion control node 54c also controls pivoting of various sections of support deck 30, such as head section 42 and, in some embodiments, one or both of thigh section 46 and foot section 48.

Motion control node 54c may also be configured to carry out one or more general operations of person support apparatus 20. Such general operations include, but are not limited to, communicating with one or more indicators, such as any one or more lights, buzzers, displays, or the like that are able to provide an indication in aural or visual form to an occupant of person support apparatus 20, or to a caregiver associated with person support apparatus 20. Motion control node 54c may also communicate with one or more sensors that are adapted to detect parameters of person support apparatus 20, such as, but not limited to, the status of a brake for wheels 24; the presence, absence, and/or movement of an occupant of person support apparatus 20 on support deck 30; the height of support deck 30 relative to base 22; the status (raised or lowered) of one or more siderails 36; the armed or disarmed state of the exit detection system, and/or other parameters. For some indicators and/or sensors, node 54c is adapted to forward information from or to one or more of these indicators and/or sensors to one or more of the other nodes 54 of control system 52.

Scale node 54d controls a scale and exit detection subsystem. The scale and exit detection subsystem includes a plurality of load cells that are positioned generally adjacent each corner of litter frame 28 and which are in direct communication with scale node 54d. The load cells sense the amount of downward weight that is exerted by an occupant of person support apparatus 20, as well as movement of the occupant. The outputs from the load cells are processed by scale node 54d to determine the total weight detected, the distribution of the weight, and/or movement of the occupant of person support apparatus 20. These determinations are forwarded to motion control node 54c, which issues any appropriate alerts based on the determinations and/or forwards the determinations to one or more other nodes 54 of control system 52 (e.g. off-board communication node 54h and/or headwall node 54i).

In at least some embodiments, scale node 54d is constructed to carry out scale and/or exit detection functions in the manner disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference. In other embodiments, scale node 54d is configured to operate in any of the manners disclosed in commonly assigned U.S. patent application Ser. No. 62/076,005 filed Nov. 6, 2014 by inventors Marko N. Kostic et al. and entitled EXIT DETECTION SYSTEM WITH COMPENSATION, or in commonly assigned U.S. patent application Ser. No. 62/065,242 filed Oct. 17, 2014 by inventors Marko N. Kostic et al. and entitled PATIENT SUPPORT APPARATUSES WITH MOTION MONITORING, the complete disclosures of both of which are hereby incorporated herein by reference. In yet another embodiment, motion control node 54c includes at least one signal acquisition node of the type disclosed in commonly assigned U.S. patent application Ser. No. 62/428,834 filed Dec. 1, 2016, by inventors Marko Kostic et al. and entitled PERSON SUPPORT APPARATUSES WITH LOAD CELLS, the complete disclosure of which is incorporated herein by reference. Still other types of scale and exit detection subsystems may alternatively be used.

Siderail node 54e is integrated into one of the right and left head end siderails 36 and siderail node 54f is integrated into the other one of the right and left head end siderails 36. Siderail nodes 54e and 54f control the occupant and caregiver user interfaces 58 and 60 integrated into that particular siderail 36. Nodes 54e and 54f forward commands entered through either of user interfaces 58 and 60 to motion control node 54c and/or to other nodes 54 of control system 52. Siderail nodes 54e and 54f also control one or more lights or other audio and/or visual indicators that are incorporated into user interfaces 58 and 60.

Wired pendant node 54g is incorporated into a pendant that is attachable to, and detachable from, person support apparatus 20. The pendant includes a cable, or other means, for coupling to control system 52 of person support apparatus 20. The pendant includes a user interface for controlling one or more aspects of person support apparatus 20. The pendant may take on a variety of different forms, such as, but not limited to, the forms disclosed in commonly assigned U.S. Pat. No. 8,413,271 issued Apr. 9, 2013, to Blanchard et al. and entitled PATIENT SUPPORT APPARATUS, the complete disclosure of which is incorporated herein by reference. Other types of pendants may be used. Still further, in some embodiments, person support apparatus 20 is not constructed to be controlled by a pendant and wired pendant node 54g is omitted.

Off-board communication node 54h controls communication between person support apparatus 20 and one or more devices that are located off-board person support apparatus 20. Off-board communication node 54h thus acts as a gateway between the on-board control system 52 and one or more external devices off-board person support apparatus 20. In many embodiments, off-board communication node 54h includes one or more wireless transceivers for wirelessly communicating with one or more external structures. In at least one embodiment, off-board communication node 54h includes a WiFi transceiver (IEEE 802.11) that enables wireless communication between person support apparatus 20 and one or more wireless access points of a local area network, such as, but not limited to, a hospital Ethernet. In some embodiments, off-board communication node 54h includes a ZigBee and/or Bluetooth transceiver for communicating with one or more medical devices, or other devices, positioned within the vicinity of person support apparatus 20. Off-board communication node 54h may also, or additionally include, one or more long-range RF transceivers and/or visible light transceivers for enabling wireless communication using visible light, such as is disclosed in more detail in commonly assigned U.S. patent application Ser. No. 62/430,500 filed Dec. 6, 2016, by inventor Michael Hayes et al. and entitled NETWORK COMMUNICATION FOR PATIENT SUPPORT APPARATUSES, the complete disclosure of which is incorporated herein by reference.

In some embodiments, off-board communication node 54h controls various aspects of a powered mattress positioned on person support apparatus 20. The powered mattress may be an inflatable mattress that contains multiple air bladders whose inflation and deflation levels are controllable via user interface 50. In some embodiments, the powered mattress is any one of the mattresses sold under the brand names Isolibrium and/or XPRT by Stryker Corporation of Kalamazoo, Mich. In some embodiments, the powered mattress includes any one or more of the features described in commonly assigned U.S. patent application Ser. No. 13/836,813 filed Mar. 15, 2013 by inventors Patrick Lafleche et al. and entitled INFLATABLE MATTRESS AND CONTROL METHODS and/or commonly assigned U.S. patent application Ser. No. 14/308,131 filed Jun. 18, 2014 by inventors Patrick Lafleche et al. and entitled PATIENT SUPPORT COVER, the complete disclosures of both of which are incorporated herein by reference. In still other embodiments, still other types of mattresses may be used. The coupling of node 54h to the mattress may be carried out via a wired or wireless connection.

When a mattress is communicatively coupled to node 54h, it transmits status and other messages to footboard node 54b that provide an indication of the current state of one or more aspects of the mattress, such as, but not limited to, the current inflation pressure of one or more sections of the mattress, the state of any therapies that are currently being provided by the mattress, and/or other information about the mattress. Some of that information is selectively displayed by footboard node 54b on a display associated with user interface 58.

Headwall node 54i communicates with one or more devices that are not physically coupled to person support apparatus 20, such as a headwall positioned within a room of a healthcare facility, a location beacon, and/or a wireless pendant. When communicating with a headwall, node 54i communicates with a nurse call interface 64 that is communicatively coupled to a conventional nurse call system. Such headwall communications thereby enable person support apparatus 20 to communicate with a conventional nurse call system that is in communication with the headwall. In the illustrated embodiment, such communication is wireless, but it may be modified in other embodiments to take place via one or more wires. Headwall node 54i is also adapted to communicate with a beacon 62 that enables the location of person support apparatus 20 to be determined. Still further, headwall node 54i may be configured to communicate with a wireless pendant used to control one or more functions of person support apparatus 20. Each of these three functions is described in more detail below.

Person support apparatus 20 determines its location within a healthcare facility by communicating with a nearby stationary beacon 62. Such communication takes place via infrared signals. Stationary beacons 62 are positioned around a healthcare facility at known locations and have a limited communication range (e.g. about 6 feet, although other ranges are possible). Further, each stationary beacon 62 has a unique ID. When installed in a healthcare facility, the locations of each of the beacons 62 are mapped so that a data table correlating the unique ID of each transceiver with the location of that particular transceiver in the healthcare facility is created. This table is used to determine the location of person support apparatuses 20. That is, when a person support apparatus 20 is able to communicate with a particular beacon 62, the person support apparatus must be in close proximity to the particular transceiver. Accordingly, the person support apparatus 20 is determined to be at the location of the particular beacon 62 that it is able to communicate with. Wireless headwall node 54*i* controls the communications between person support apparatus 20 and beacon 62.

In one embodiment, beacon 62 transmits its unique ID to person support apparatus 20, which receives it at node 54*i*. Control system 52 forwards this unique ID, along with an ID number corresponding to the unique identity of that person support apparatus, to a healthcare local area network (LAN). A server on the healthcare LAN contains the data table that correlates all of the beacon 62 IDs to their respective locations within the healthcare facility. By utilizing this table, the server looks up the particular beacon ID in the table and determines that the particular person support apparatus 20 (the one whose ID was transmitted with the beacon ID) that transmitted the beacon ID is at the same location as the beacon 62. In another embodiment, the data table containing the locations of all of the beacons 62 and their respective locations within the healthcare facility is downloaded to each person support apparatus 20 and stored in its internal memory. One of the nodes 54 on person support apparatus 20 then utilizes this table to determine the location of person support apparatus 20 within the healthcare facility. This location is then used in some communications between person support apparatus 20 and servers or other devices on the healthcare LAN. In still other embodiments, node 54*i* and stationary beacon 62 can be modified to function in any of the manners disclosed in commonly assigned U.S. Pat. No. 8,674,826 issued to Becker et al. and entitled LOCATION DETECTION SYSTEM FOR A DEVICE, the complete disclosure of which is hereby incorporated herein by reference.

Headwall node 54*i* also provides communication between person support apparatus 20 and a conventional nurse call system by using, in at least one embodiment, a standard 37 pin nurse call cable adapted to communicate with a nurse call system interface 64. In addition to transmitting voice signals to and from the nurse call system, the standard 37 pin cable may further transmit alert information (e.g. whether an exit alert has been triggered or not), and/or other information to the nurse call interface 64.

In the embodiment shown in FIG. 2, headwall node 54*i* uses wireless communication between person support apparatus 20 and the conventional nurse call system by using a Bluetooth transceiver adapted to wirelessly communicate with nurse call system interface 64. A more detailed description of several manners in which headwall node 54*i* may wirelessly communicate with nurse call system interface 64 is disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of headwall communication may also be implemented.

Headwall node 54*i* is also adapted to communicate with wireless pendant node 54*p*, in at least some embodiments. In some embodiments, node 54*i* communicates with wireless pendant node 54*p* using the I-Squared-C communication protocol transmitted over a wireless medium, while in other embodiments, node 54*i* is configured to communicate with wireless pendant node 54*p* using a different communication protocol.

A propulsion motor control node 54*j* may be included as part of control system 52. In the embodiment of person support apparatus 20, propulsion motor control node 54*j* controls a motor that powers and, in some cases, steers one or more of wheels 24, thereby easing the physical load otherwise experienced by a caregiver when moving person support apparatus 20 from one location to another. In alternative embodiments, person support apparatus 20 includes a separate wheel positioned generally in the middle of base 22 that is powered. Such powered wheels are disclosed in commonly assigned U.S. patent application Ser. No. 62/315,067 filed Mar. 30, 2016, by inventors Thomas Puvogel et al. and entitled PATIENT SUPPORT APPARATUSES WITH DRIVE SYSTEMS, the complete disclosure of which is incorporated herein by reference. In alternative embodiments, propulsion motor control node 54*j* controls the motors for any of the propulsion systems disclosed in commonly assigned U.S. patent application Ser. No. 13/795,193, filed Mar. 12, 2013, by inventors Richard Derenne et al. and entitled POWERED PATIENT SUPPORT APPARATUS, and/or in U.S. Pat. No. 6,772,850 issued to Waters et al. and entitled POWER ASSISTED WHEELED CARRIAGE, the complete disclosures of both of which are hereby incorporated herein by reference. Other types of on-board propulsion systems may also be controlled by propulsion motor control node 54*j*.

When propulsion motor control node 54*j* is included, a propulsion interface node 54*k* is also provided that controls and oversees a propulsion user interface (not shown). The propulsion user interface includes the controls used by a person to operate the propulsion system. In some embodiments, the user interface includes a pair of handles having force sensors that detect forces applied by a user. One example of such handles and force sensors are disclosed in the aforementioned commonly assigned 62/315,067 patent application. Propulsion interface node 54*k* senses the magnitude and, in some cases the direction, of the applied forces and sends messages indicating the sensed magnitudes and directions to propulsion motor control node 54*j*. Motor control node 54*j*, in response, sends motor controls commands to the one or more propulsion motors.

Each of nodes 54*a, b, c, d, h, i, j*, and *k* includes a controller (e.g. controller 70*a* of FIG. 3) that controls the operation of the node. Such controllers are implemented, in at least one embodiment, as conventional microcontrollers. In one example, the controllers are implemented as any one of the i.MX family of system-on-chip (SoC) processors which are marketed by Freescale Semiconductor of Austin, Tex. Other types of commercially available microcontrollers may also be used. Still further, the controllers may take on still other forms, such as any combination of any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by the controllers in carrying out the functions described herein, as well as the data necessary for carrying out these functions, are stored in one or more accessible memories (not shown).

Nodes 54a-k communicate with each other over a plurality of different types of communication media 56. The communication media 56 correspond to the physical layers (layer 1) of the Open Systems Interconnection (OSI) Model, such as the wires, cables, cords, fiber optics, etc. that are defined by these physical layers, as well as the shapes and properties of the electrical connectors, the broadcast frequencies, modulation scheme, and other low level parameters. In the embodiment shown in FIG. 2, media 56 include media for supporting one or more Ethernet connections 56a, one or more Controller Area Network (CAN) connections 56b, one or more RS-485 connections 56c, and one or more I-Squared-C (I²C) connections 56d.

The Ethernet connections 56a conform to any one of the various Ethernet physical layer specifications (e.g. 100BASE-T, 100BASE-TX, 100BASE-LX, 1000BASE-T, 1000BASE-T1, 1000BASE-TX, etc.). In at least one embodiment, the physical media used to implement each connection 56a of the Ethernet 66 is twisted pair copper wire. In another embodiment, the physical media used to implement each connection 56a of the Ethernet 66 is fiber optic cables. In still other embodiments, Ethernet 66 includes some connections 56a that are defined by a first physical media (e.g. twisted pair copper wire, fiber optic cables, etc.) and some other connections 56a that are defined by a second physical media that is different from the first physical media. Still further, in some embodiments, the data transmission rates over connections 56a are not uniform across all connections 56a. For example, in some embodiments, some connections 56a are configured as 10BASE-T while others are configured as 100BASE-T.

The CAN connections 56b conform to any one of the physical layer standards set forth in any of the ISO 11898 standards (e.g. ISO 11898-2:2003; ISO 11898-5:2007; ISO-11898-6:2013, etc.). The RS-485 connections 56c conform to the Telecommunications Industry Association and Electronic Industries Alliance (TIA/EIA) RS-485 standard (a.k.a. TIA-485), including full-duplex communication. The I-Squared-C connections 56d conform to the multi-master, multi-slave, singled-ended, serial computer bus of the same name invented by Philips Semiconductor.

It will be understood that the combination of the four particular media 56 discussed above are merely illustrative of one embodiment of the present disclosure. In other embodiments, control system 52 may add one or more different communication media 56, use less than four different media types, and/or substitute one or more of the aforementioned media with one or more other types of media. Such other media include, but are not limited to, media for supporting a Local Interconnect Network (LIN) bus, Firewire, RS-232, a Universal Serial Bus (USB), RS-422, a LONWorks bus, and/or a Serial Peripheral Interface (SPI) bus.

Ethernet connections 56a and their connected nodes 54 define an onboard Ethernet 66. Onboard Ethernet 66 includes an Ethernet switch 68 in the embodiment of control system 52 shown in FIG. 2. Ethernet switch 68 routes messages back and forth between nodes 54a, 54c, 54h, 54j, and 54i. Ethernet switch 68 may comprise its own separate node 54, or it may be integrated into any one or more of the other nodes 54a-i. The nodes coupled to Ethernet switch 68 are able to communicate with each other using an Ethernet protocol. Although Ethernet switch 68 is shown in FIG. 2 coupling nodes 54a, 54c, 54h, 54j, and 54i together in a star topology, it will be understood that other network topologies can be implemented in one or more of the embodiments disclosed herein, including ring topologies, combinations of ring and star topologies, and still others. In at least one embodiment, Ethernet switch 68 operates in any of the manners described in commonly assigned U.S. patent application Ser. No. 14/622,221 filed Feb. 13, 2015, by inventors Krishna Bhimavarapu et al. and entitled COMMUNICATION METHODS FOR PATIENT HANDLING DEVICES, the complete disclosure of which is hereby incorporated herein by reference. Ethernet switch 68 may operate in still other manners.

One or more of the nodes 54 are adapted to communicate messages over a plurality of different types of communication media 56 using a plurality of types of communication protocols. For example, node 54a of control system 52 is adapted to communicate messages over an Ethernet medium 56a, a Controller Area Network (CAN) medium 56b, and an RS-485 medium 56c. The particular communication protocols used by node 54a when sending messages over these communication media 56a, 56b, and 56c will be discussed in greater detail below. Node 54c, as another example, is adapted to communicate messages over four different types of communication media using at least three different types of communication protocols, further details of which are provided below. Other nodes of control system 52 may be adapted to only communicate over two different types of media, or only a single type of medium (e.g. node 54b: RS-485 medium 56c).

The particular messages communicated over the various media 56 convey a plurality of different types of information. In general, the messages includes any commands, sensors readings, status information, alerts, and/or other types of data that are generated or used by any of the nodes 54 when carrying out the functions described above. Messages are thus transferred between nodes 54 when a user or caregiver pushes a button (or otherwise activates a control) that moves a component of person support apparatus 20, when a caregiver changes one or more settings of person support apparatus 20 (e.g. arms or disarms the exit detection system, takes a weight reading, locks out a patient's motion control interface, etc.), when new readings are taken from one or more sensors, and/or when other information needs to be communicated. Regardless of the specific content of the messages, the messages are transmitted between nodes 54 as one or more packets.

In some embodiments, the particular messages transmitted over the various media 56 are divided according to their level of safety-relatedness. For example, messages relating to motor control and/or other features that could impact the safety of person support apparatus 20 are sent over a deterministic communication medium 56 via a deterministic protocol, such as a CAN message sent over an RS-485 medium 56c. Messages having lower levels of safety criticality may be sent over Ethernet medium 56a using any of various message protocols. Still further, in some embodiments, safety-critical messages can be sent over multiple communication media 56 (using the same or different higher level protocols) to an intended recipient node, thereby increasing the likelihood that the important message is timely received at the recipient node.

In general, and as will be described in more detail below, one or more of nodes 54 of control system 52 are configured to convert one or more packets formulated according to a layer 3 (or higher) protocol (e.g. IP, TCP, FTP, a non-standard layer 3 protocol, etc.) into multiple different layer 2 (or lower) formats or protocols (e.g. Ethernet frames, CAN packets, non-standard packets, etc.). Further, one or more nodes 54 of control system 52 are adapted to convert one or more packets formulated according to a layer 2 (or higher) protocol (e.g. Ethernet frame, CAN packet, a non-standard packet) into a different layer 2 format or protocol (e.g. Ethernet frame, CAN packet, a non-standard packet). Still further, one or more nodes 54 of control system 52 are adapted to transmit a specific type of layer 2 packet over different physical layers, as well as to transmit different types of layer 2 packets over a common physical layer. The packets contain, either wholly or partially, data that defines various messages communicated between the nodes 54. The messages include not only messages regarding the operation of the various components of person support apparatus 20, but also messages used for setting up and maintaining the communication functions between the nodes 54 (e.g. setting baud rates for RS-485 and/or I-Squared-C media; sharing addresses, transmitting heartbeat messages, notifying nodes 54 of the addition, removal, and/or malfunction of other nodes 54, etc.).

Figure 3:
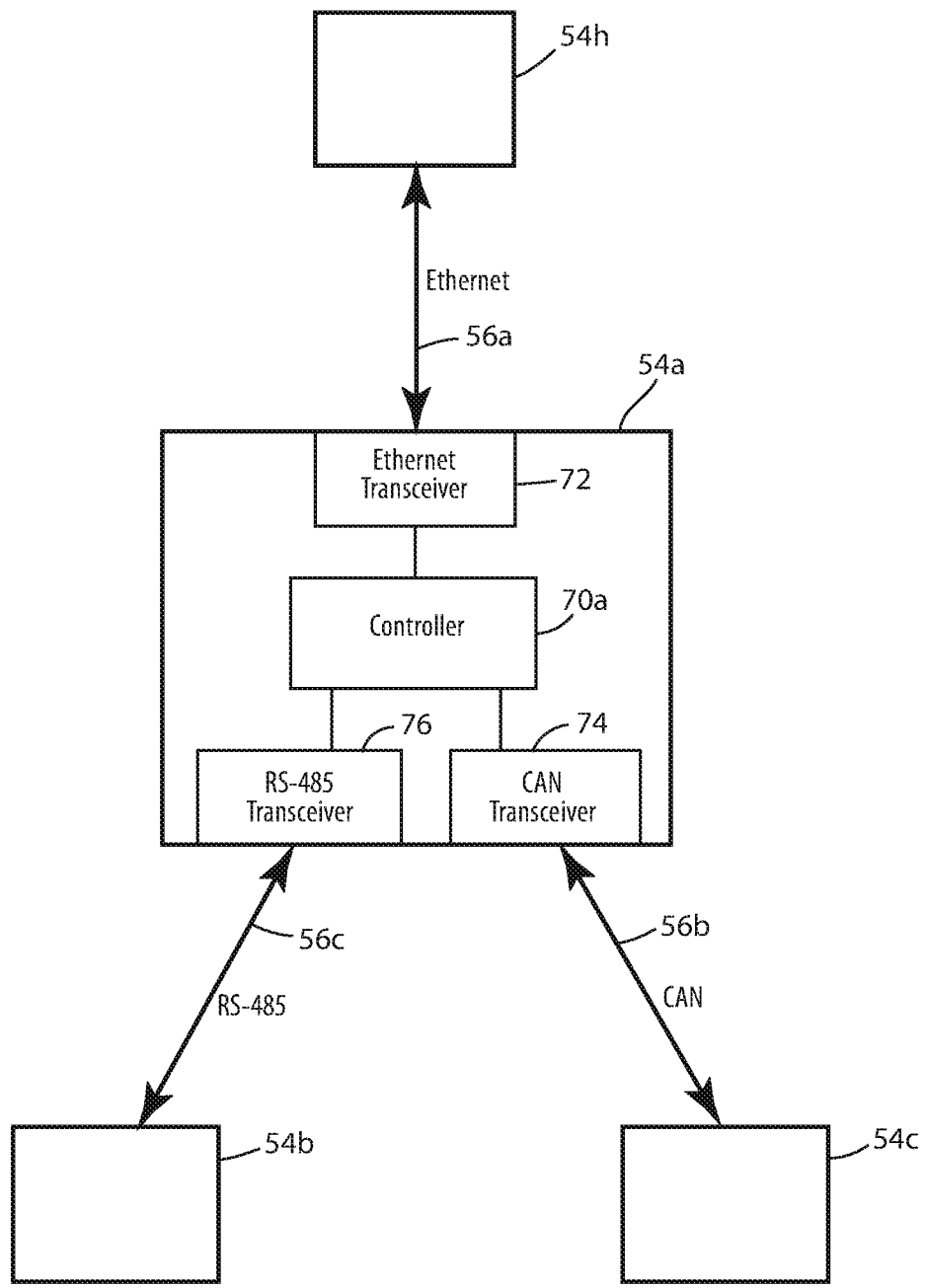
FIG. 3 is a block diagram of an exemplary node from the control system of FIG. 2.

FIG. 3 illustrates a block diagram of graphics engine node 54a. The detailed operation of formulating and reformulating packets performed by graphics engine node 54a will now be described in more detail below. It will be understood that this description of graphics engine node 54a applies to all of the other nodes 54 disclosed herein that communicate over multiple communication media 56 and/or that convert packets from one format into another.

Graphics engine node 54a is coupled to three different media 56: an Ethernet medium 56a, a CAN medium 56b, and an RS-485 medium 56c. Other nodes 54 that include connections to an Ethernet medium 56a, a CAN medium 56b, and an RS-485 medium 56c (e.g. node 54c and propulsion motor control node 54j) operate in the exact same manner as node 54a, as is discussed in more detail below. Those nodes that have connections to less than three media 56, or that do not convert packets between as many different formats as node 54a, may be programmed with less functionality than node 54a, or they may be programmed with the same capability to perform this functionality but not necessarily use all of the functionality that node 54a is capable of. That is, those nodes of control system 52 having fewer than three wired connections, such as node 54i, 54d-g, etc., operate in a similar manner as nodes 54a, c, and j, but translate message packets between a smaller subset of formats for forwarding over a smaller subset of communication media 56 (e.g. node 54h translates messages between Ethernet and whatever wireless communication protocol (e.g. WiFi) is being used to communicate with one or more off-board structures (e.g. a wireless access point of a local area network)).

Graphics engine node 54a includes a node controller 70a, an Ethernet transceiver 72, a CAN transceiver 74, and an RS-485 transceiver 76. As noted previously, controller 70a is a conventional microcontroller in at least one embodiment, although it may take on other forms, including any combination of any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Transceivers 72-76 may be conventional, commercially available integrated circuits that interface with, and provide access to, the respective communication media 56. In those nodes having a connection to a different communication medium (e.g. I-Squared-C), a different transceiver is included within the node for accessing and controlling interactions with that particular communication medium.

Graphics engine node 54a of FIG. 3 has been illustrated with simplified connections in order to more easily describe its communication functions. Thus, node 54a is shown in FIG. 3 as being connected to only one node (arbitrarily selected as node 54h) via an Ethernet medium 56a when in fact node 54a is coupled in control system 52 (via switch 68, as shown in FIG. 2) to four different nodes. Similarly, node 54a is coupled to two other nodes via a CAN medium 56b (as shown in FIG. 2), but has been shown in FIG. 3 as only coupled to a single node (arbitrarily selected as node 54c). These simplifications have been done in FIG. 3 to both more clearly illustrate the manner in which the nodes of control system 52 communicate, as well as to reinforce the fact that the particular connections between nodes 54 can be changed from what is illustrated in FIG. 2, including the number of nodes, the functions of the nodes, and both the types and numbers of communication media 56 to which the nodes 54 are coupled.

Graphics engine node 54a, as well as the other nodes 54 of control system 52, is configured to communicate with other nodes 54 using messages that are defined in accordance with multiple protocols. Thus, if graphics engine node 54a receives a message from Ethernet medium 56a, the message will be defined in accordance with a first communication protocol (e.g. an Ethernet protocol, an Internet Protocol (IP), a Transport Control Protocol (TCP), a User Datagram Protocol (UDP), and/or another protocol). If the message is not destined for node 54a, controller 70a of node 54a converts the message to another protocol. After conversion to the other protocol, the converted message is forwarded to the intended recipient (or another intermediary node on the way to the intended recipient) over one of the other communication media (56b and 56c).

In some embodiments, the multiple protocols that the nodes 54 are capable of processing include at least one non-standard protocol. Such non-standard protocols include protocols that are not publicly known, as well as protocols that may be known but are not supported by generally available hardware. Further, the non-standard protocols refer to protocols that include different layers of the OSI model (e.g. layers 2, 3, and/or 4). In many cases, the non-standard protocols are proprietary protocols, although this need not necessarily be so. Such non-standard protocols may be especially designed for use with a particular product (e.g. a specific model of a person support apparatus 20), a type of product (e.g. multiple types of person support apparatuses 20), and/or a group of multiple types of products (e.g. patient care devices). Control system 52, as will be discussed more below, allows the mixing of such non-standard protocols over various communication media 56 with little or no modification to the underlying programming of the nodes, thereby allowing legacy-designed products to be upgraded and/or incorporated into newer designs that utilize one or more standard communication protocols and/or media 56.

Figure 4:
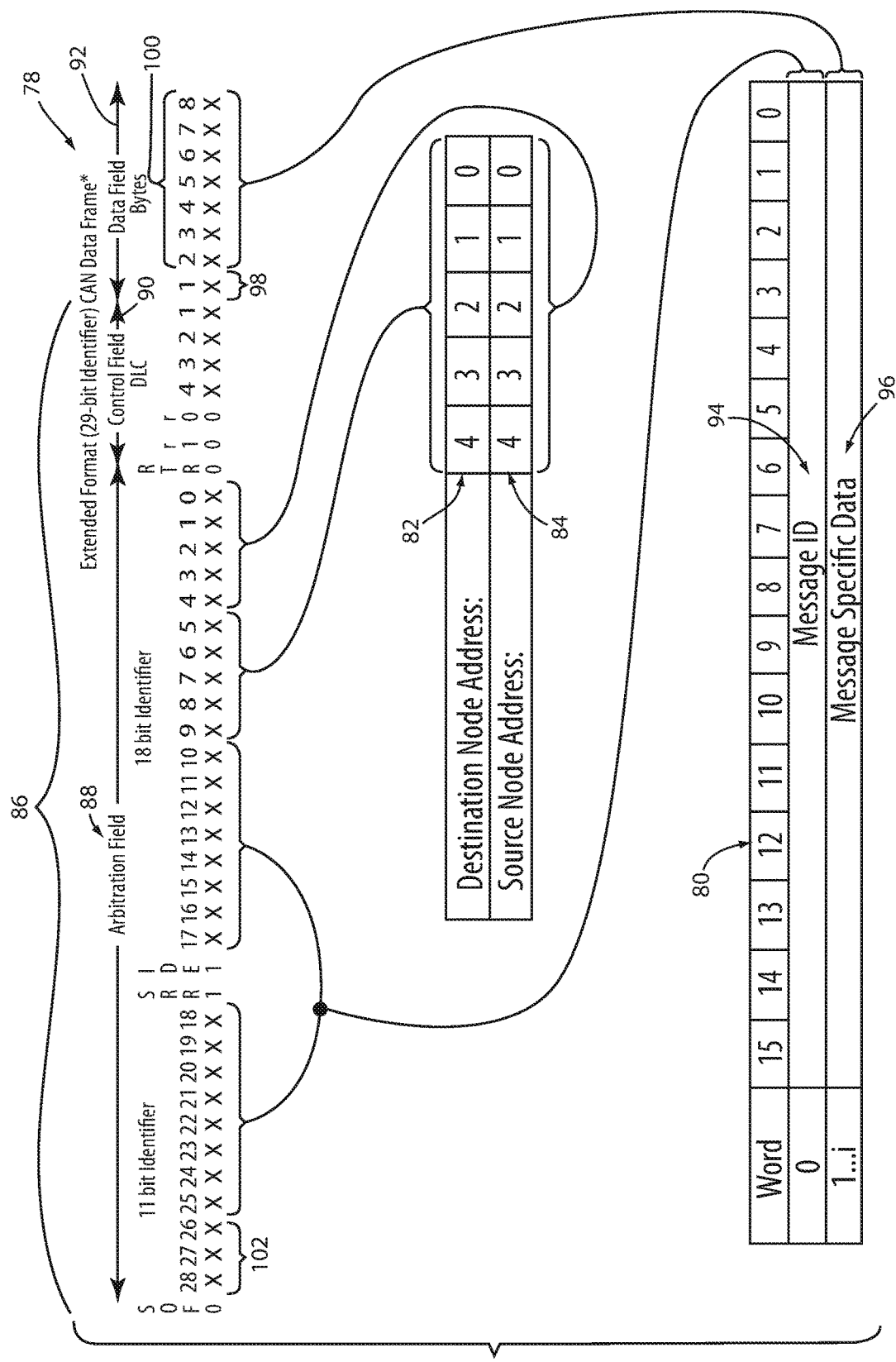
FIG. 4 is a diagram showing an illustrative manner in which a node of the control system converts messages between a first protocol and a Controller Area Network (CAN) protocol.

FIG. 4 illustrates in more detail one manner in which controller 70a converts messages between a first protocol and a second protocol for transmission over communication media 56. FIG. 4 illustrates a conventional CAN packet 78, a message 80 defined according to a non-standard protocol, a destination address 82, and a source address 84. CAN packet 78 includes a header 86 comprising an arbitration field 88 and a control field 90. CAN packet 78 also includes a data field or payload 92. Payload 92 comprises 8 octets (bytes) while arbitration field 88 comprises thirty-one bits. Control field 90 comprises six bits. CAN packet 78 is arranged as a conventional extended frame packet having a 29 bit identifier (CAN 2.0B) rather than an 11 bit identifier (e.g. CAN 2.0A). It will be understood, however, that the controllers (e.g. 70*a*) of control system 52 can be modified to process CAN packets having 11 bit identifiers. CAN packet 78 corresponds to the data link layer of the OSI model.

If node 54*a* receives CAN packet 78 from another node (e.g. node 54*c*) that is destined for yet another node (e.g. node 54*h*), controller 70*a* converts the CAN packet 78 to a packet or message in accordance with another protocol (e.g. a non-CAN protocol). In the embodiment illustrated in FIG. 4, controller 70*a* converts CAN packet 78 to a message 80 having a non-standard protocol. The non-standard protocol uses a message format in which the first sixteen bits define a message ID field 94. The subsequent bits of message 80 define a message data field 96. The message data field 96, in the illustrated embodiment, has a variable length that is at least sixteen bits long.

Controller 70*a* also extracts the destination node address 82 and the source node address 84 from CAN packet 78. Both the destination and source addresses 82 and 84 are five bit addresses in the illustrated embodiment, and each node 54 includes such a unique five bit address, although it will be understood that other address lengths can be used. Source address 84 identifies the address of the original sender of a message. Destination address 82 identifies the address of the node 54 that is ultimately intended to receive packet 78.

As shown in FIG. 4, controller 70*a* extracts the source address 84 from the first five bits of the 18 bit identifier subfield of arbitration field 88 (i.e. bits 0-4 of this subfield). Controller 70*a* extracts the destination node address 82 from the next five bits of the 18 bit identifier subfield of arbitration field 88 (i.e. bits 5-9 of this subfield). Controller 70*a* extracts the message ID 94 from the next eight bits of the 18 bit identifier subfield of arbitration field 88, as well as the first eight bits of the 11 bit identifier subfield of arbitration field 88. Controller 70*a* also extracts the message data that goes into the $3^{rd}$ and 4th octets (and possibly subsequent octets) of message 80 from the payload 92 of CAN packet 78. Controller 70*a* only moves data from a subgroup 100 of the eight bytes of payload 92 into message 80. In the illustrated embodiment, the subgroup 100 includes seven of the eight bytes of payload 92. The remaining byte 98 of payload 92 is used by control system 52 to indicate whether or not CAN packet 78 contains a complete message within payload 92 or only a portion of a message. If payload 92 does not contain a complete message, then multiple CAN packets 78 must be received before message 80 can be completely defined. If payload 92 does contain a complete message, however, then only a single CAN packet 78 is needed to generate message 80 from that CAN packet 78.

In some embodiments, the remaining byte 98 of payload 92 contains a counter that indicates how many other packets 78, if any, are to be grouped into a single message 80. Thus, if CAN packet 78 is a standalone packet, remaining byte 98 contains a zero. If it is only a portion of a message that is being sent as a grouping of CAN packets, then remaining byte 98 contains a number corresponding to the number of CAN packets 78 in that group. Because remaining byte 98 is eight bits long, control system 52 is able to piece together up to two hundred and fifty-six CAN packets 78 ($2^8$) into a single message 80. The data from the subgroups 100 contained within each of the CAN packets 78 is moved into the message specific data field 96 of message 80.

In some alternative embodiments, remaining byte 98 is used as both a counter and for other purposes. In such embodiments, a first subgroup of the eight bits of byte 98 indicates what number a particular CAN packet 78 has been designated within a sequence of CAN packets 78 (zero if the CAN packet 78 is a standalone packet), and a second subgroup of the eight bits indicates other information, such as, but not limited to, different flags indicating whether an error has occurred, or a node is busy, or still other information.

Message ID field 94 of message 80 identifies what type of message is being transmitted between nodes. In one embodiment, message 80 uses a non-standard communication protocol in which several different types of predefined messages are used, such as, but not limited to, the following: a protocol version request, a protocol version response, a property list request, a property list response, a get value request, a get value response, a set value request, a set value response, a get range request, a get range response, a subscribe request, a subscribe response, an unsubscribe request, an unsubscribe response, a renew subscription request, a renew subscription response, and a subscription stream. Still other types of predefined message types may also or alternatively be used. Each of these message types is assigned a unique sixteen bit identifier in the embodiment shown in FIG. 4. The sixteen bit identifier is stored within message ID field 94. The contents and meaning of the data contained within message data field 96 is determined by a node based upon the particular type of message identified in the message ID field 94. It will be understood that message ID field 94 can take on other lengths besides the sixteen bits illustrated herein.

As set forth above, the different types of messages identified in message ID field 94 correspond to two different general types: requests and responses (with the sole exception of the "subscription stream" message, which will be discussed below). The request messages request certain information from another node. The requested information is identified by the name of the message. For example, a "protocol version request" message asks a node to respond with information identifying what "protocol version" that node is currently using for communication. The protocol version defines how the content and order of the content within message data field 96 is to be interpreted.

The "subscribe request" message is another example of the types of messages 80 that may be sent between nodes. The "subscribe request" message requests that the recipient node treats the requesting node as having a subscription to one or more pieces of data that are generated by the recipient node. Any nodes that have a subscription to specific data automatically receive updates to the data to which they are "subscribed" from the source of that data without having to specifically request the data. The other "request" messages are self-explanatory from their titles. The "response" messages are sent in response to the "request" messages and acknowledge the request, contain the requested data (if any), and/or indicate if any errors or other problems are present in performing the requested action.

The subscription stream message is sent whenever the conditions described in a subscription request are met. The subscription stream message contains within its payload a current snapshot of all of the values gathered by a particular node. The request, response, and subscription stream messages are, in at least one embodiment, part of a non-standard communication protocol used by the nodes 54.

The foregoing description of how controller 70a converts CAN packet 78 into message 80 is also applicable to how controller 70a converts a message 80 into a CAN packet 78. That is, if node 54a receives a message 80 from either RS-485 communication medium 56c or Ethernet medium 56a and the message has a destination address of a node reachable via CAN communication medium 56b, controller 70a converts the incoming message into one or more CAN packets 78. Controller 70a then sends the CAN packets to CAN transceiver 74 for forwarding along CAN communication medium 56b.

Controller 70a converts messages 80 into one or more CAN packets 78 in a process that is the reverse of that described above. More specifically, controller 70a extracts the message ID 94 from message 80 and places those sixteen bits into the 18 bit and 11 bit identifier fields of packet 78 in the locations shown. Eight bits of the message ID 94 are placed in the bits labeled 10-17 in the 18 bit identifier field of FIG. 4, and the eight remaining bits of the message ID 94 are placed in the bits labeled 18-25 in the 11 bit identifier field of FIG. 4. The particular eight bits (most significant versus least significant) selected for inclusion in the 18 bit and 11 bit identifiers of CAN packet 78 can be configured as desired.

Controller 70a also converts incoming messages 80 into CAN packets 78 by extracting up to seven bytes worth of data from the message data field 96 of message 80. Controller 70a places these seven bytes into the subgroup 100 of payload 92 of CAN packet 78. If message 80 contains more than seven bytes worth of data within message data field 96, then controller 70a converts the message 80 into multiple CAN packets 78. When converting a single message 80 into multiple CAN packets 78, controller 70a inserts an identifier (e.g. a sequence number, or the like) into remaining byte 98 of the CAN packets that enables the recipient to piece together the multiple CAN packets 78 into a single message 80.

Controller 70a also adds the destination address 82 and source address 84 to the bits labeled 0-4 and 5-9, respectively, in the 18 bit identifier field of FIG. 4. Although message 80 does not itself include a destination address 82 and a source address 84, this information is transmitted with message 80. That is, in the illustrated embodiment, message 80 is never transmitted in the naked format shown in FIG. 4, but instead is encapsulated and/or otherwise incorporated into one or more data structures defined by lower layers, and those lower layer data structures include the destination and source addresses 82 and 84. Thus, if message 80 is received from another node, message 80 will be received as part of a larger packet that includes the destination and source address, and controller 70a will extract this information and place it into CAN packet 78. On the other hand, if message 80 originates from node 54a, controller 70a determines the destination address 82 itself and retrieves the source address (the address of node 54a itself) from a memory of node 54a.

When sending a CAN packet 78, controller 70a of node 54a also adds a three bit arbitration field 102 to the CAN packet 78. As shown in FIG. 4, arbitration field 102 is added to the three bits labeled 26-28 in the 11-bit identifier field. The content of arbitration field 102 is determined by controller 70a based upon the message ID 94. That is, controller 70a is programmed to assign different priorities to different messages having different ID's 94. The specific priorities that are assigned are chosen by the programmer based upon the desired design and/or functionality of person support apparatus 20. In accordance with the CAN standards, messages having the highest priority have arbitration field 102 populated with three zeros, while messages having the lowest priority have arbitration field 102 populated with three ones.

Figure 5:
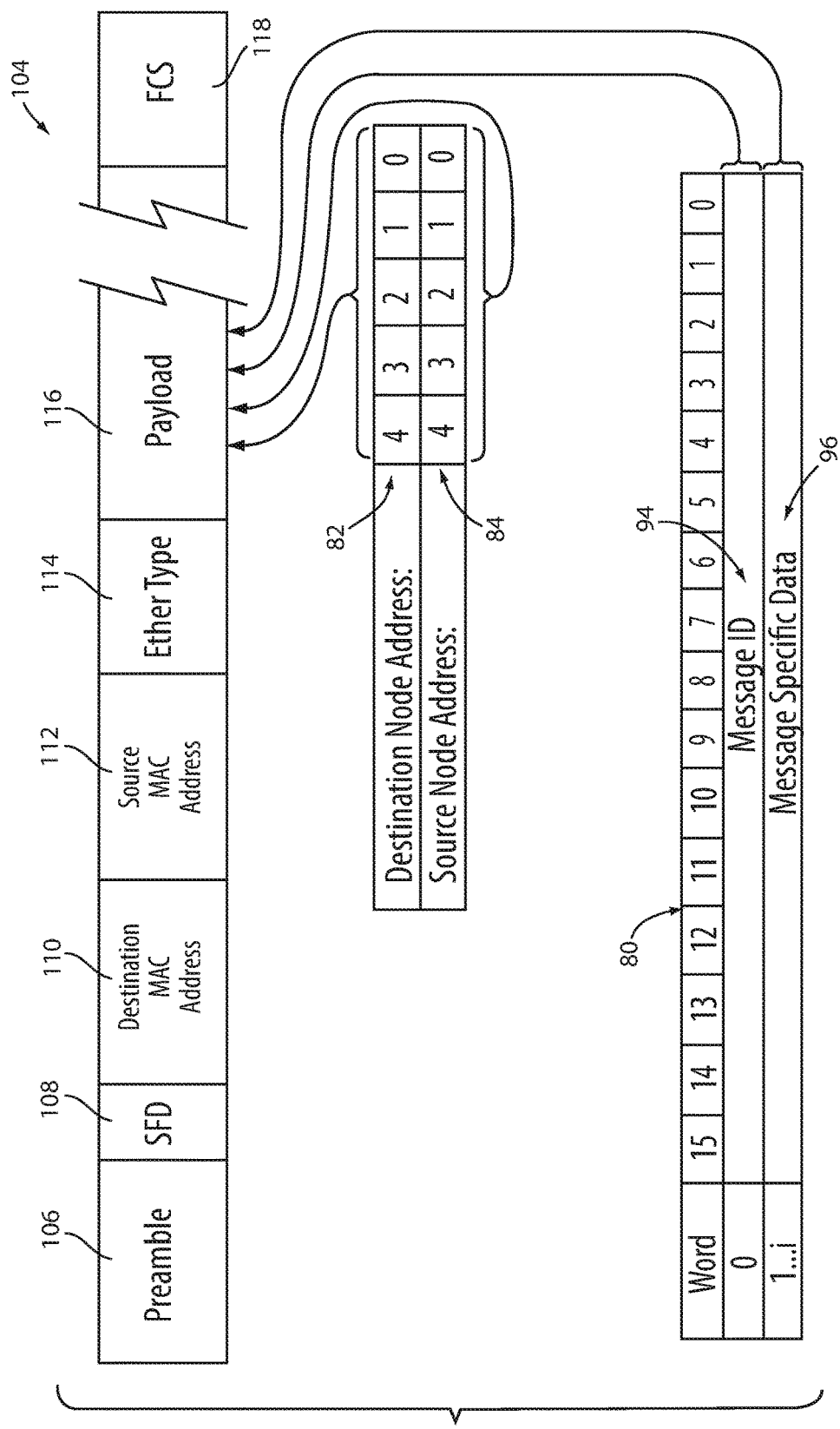
FIG. 5 is a diagram showing an illustrative manner in which a node of the control system converts messages between the first protocol and an Ethernet protocol.

FIG. 5 illustrates in more detail one manner in which controller 70a converts messages between an Ethernet protocol and the protocol of message 80. FIG. 5 illustrates a conventional Ethernet frame 104, a message 80 defined according to the same non-standard protocol discussed above with respect to FIG. 4, and destination and source addresses 82 and 84. Ethernet frame 104 corresponds to the data link layer of the OSI model and includes the normal fields of a conventional Ethernet frame. These fields includes a preamble 106, a start of frame delimiter (SFD) field 108, a destination MAC address field 110, a source MAC address field 112, an Ether type field 114, a payload 116, and a frame check sequence (FRC) field 118.

When an Ethernet frame 104 is received by a node, such as node 54a, the controller of that node (e.g. controller 70a) extracts message 80 from the payload 116 of the Ethernet frame. The payload 116 may be up to 1500 octets long. As such, payload 116 is typically large enough to include not only the entire message 80, but also the destination and source addresses 82 and 84. If message 80 is longer than can fit within payload 116 of Ethernet frame 104, then multiple Ethernet frames 104 are sent and controller 70a reconstructs a single message 80 from the multiple Ethernet frames 104.

If a node, such as node 54a, receives message 80 from a non-Ethernet communication medium 56 and, after examining the destination address 82, determines that the address is reachable through Ethernet medium 56a, controller 70a converts the message 80 to one or more Ethernet frames 104. Controller 70a converts messages 80 to Ethernet frames 104 by simply placing the entire message 80, as well as the destination and source addresses 82 and 84, into the payload 116 of the Ethernet frame 104 (assuming it will fit). If the message 80 is too large to go into a single Ethernet frame 104, then controller 70a breaks the message 80 into pieces that are each small enough to fit into the payloads of Ethernet frames 104.

Figure 6:
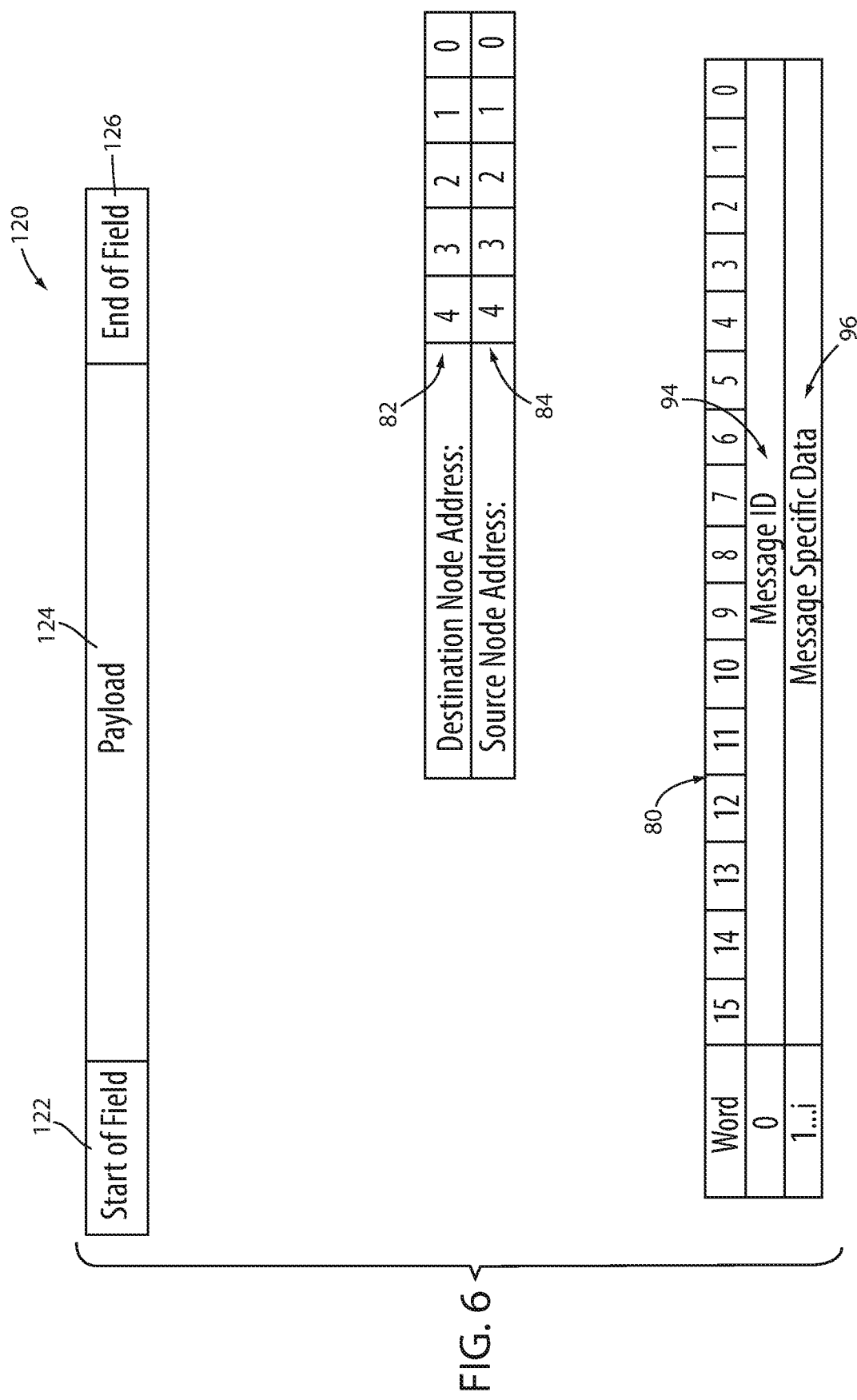
FIG. 6 is a diagram showing an illustrative manner in which a node of the control system converts messages between the first protocol and a serial protocol.

FIG. 6 illustrates in more detail one manner in which controller 70a converts messages between an RS-485 protocol and the protocol of message 80. FIG. 6 illustrates a packet 120 adapted to be transmitted over an RS-485 communication medium 56c. Packet 120 corresponds to the data link layer of the OSI model and includes a start of field header 122, a payload 124, and an end of field trailer 126. Packet 120 may also or alternatively include other fields beside the three shown in FIG. 6. Such additional or alternative fields include a checksum field, a sequence number field, and other fields.

The specific content of header 122 and trailer 126 may vary from embodiment to embodiment, and packet 120 may be formatted according to a non-standard protocol. Alternatively, packet 120 may be formatted according to a standard layer 2 protocol. In some embodiments, the payload of packet 120 is an encapsulated Ethernet frame 104 or an encapsulated CAN packet 78. Further, because the RS-485 standards are standards for the physical layer, rather than higher layers, in some embodiments, the entire packet 120 can formulated as an Ethernet frame 104 or a CAN packet 78 that is simply sent over an RS-485 communication medium 56c, rather than an Ethernet medium 56a or a CAN medium 56b.

When a packet 120 is received by a node, such as node 54*a*, the controller of that node (e.g. controller 70*a*) extracts message 80 from the payload 124 of the packet 120. The payload 124, in some embodiments, has a length that is user-defined. As such, payload 124 is typically large enough to include not only the entire message 80, but also the destination and source addresses 82 and 84. If message 80 is longer than can fit within payload 124 of packet 120, then multiple packets 120 are sent and controller 70*a* reconstructs a single message 80 from the multiple packets 120.

If a node, such as node 54*a*, receives message 80 from a non-RS-485 communication medium 56 and, after examining the destination address 82, determines that the address is reachable through an RS-485 medium 56*c*, controller 70*a* converts the message 80 to one or more packets 120. Controller 70*a* converts messages 80 to packets 120 by simply placing the entire message 80, as well as the destination and source addresses 82 and 84, into the payload 124 of packet 120 (assuming it will fit). If the message 80 is too large to go into a single packet 120, then controller 70*a* breaks the message 80 into pieces that are each small enough to fit into the payloads of the packets 120.

Although not illustrated in the drawings, packet 120 may also be used when sending messages over an I-Squared-C communication media 56*d*. That is, in one embodiment, the node controllers are adapted to send messages 80 over both RS-485 communication media 56*c* and I-Squared-C communication media 56*d* using the same format of packet 120.

FIGS. 4-6 illustrate the ways in which a node controller converts a message 80 to a CAN packet 78, an Ethernet frame 104, and a packet 120. These FIGS. also illustrate the reverse process: how a node controller converts a CAN packet 78, an Ethernet frame 104, and a packet 120 to a message 80. Still further, FIGS. 4-6 illustrate how nodes are able to convert messages from CAN to Ethernet, or CAN to RS-485, Ethernet to RS-485, or vice versa. For example, if a node receives a CAN message that is to be converted to an Ethernet frame, the node may follow the process illustrated in FIG. 4 and convert the CAN message to a message 80, and then subsequently convert the message 80 to an Ethernet frame in the manner illustrated in FIG. 5. In alternative embodiments, the node may directly convert between CAN, Ethernet, and RS-485 messages without converting the messages to the format of message 80 between these conversions.

When a message 80 is to be sent from a source node of control system 52 to a destination node, the source node controller assembles the message into whatever format is used with the initial link (i.e. communication medium 56). In other words, the source node controller assembles the message 80 into an Ethernet frame 104 if the initial link is an Ethernet medium 56*a*, a CAN packet 78 if the initial link is a CAN communication medium 56*b*, or a packet 120 if the initial link is an RS-485 medium 56*c* or an I-Squared-C medium 56*d*. The node controller adds the five bit address of itself (source address 84), as well as the five bit address of the destination (destination address 82) based upon a table that is stored within each node during the initial set up of control system 52. The table includes the addresses of each node in control system 52. The table is stored in the memory of each of the nodes and, in some embodiments, automatically generated during the initialization of control system 52.

After the message is assembled into the corresponding format and addressed to its correct destination node, it is forwarded to the transceiver for that initial link and sent by the transceiver to a first node. If the first node is not the destination node, the first node forwards the message 80 to another node that is either the destination node or a second node that is intermediate the first node and the destination node. If this forwarding requires sending the message over a different communication medium and/or in a different format used by the nodes for that particular link, the first node controller converts the message 80 to the format corresponding to the different communication medium. The conversion is done in one of the manners discussed above with respect to FIGS. 4-6. If the receiving node is not the final recipient, then any necessary further conversion of the message takes place and the message is forwarded once again. This process repeats until the message reaches its final destination. The node controller of the final destination processes the message and reacts accordingly based on the data contained within the message specific data field 96.

Although not illustrated in the drawings, any one or more of the nodes 54 may be programmed to convert or reformulate other messages formats for transmission over the various communication media 56. For example, in some embodiments, one or more of the nodes 54 are programmed to send Transport Control Protocol (TCP) and/or Internet Protocol (IP) packets over any of the various media 56 disclosed herein. When sending TCP and/or IP packets over an Ethernet medium, very little reformulation is necessary as such packets can typically be completely encapsulated within payload 116 of an Ethernet frame 104. When sending TCP and/or IP packets over a CAN medium 56*b*, however, such packets will typically need to be broken up and sent as multiple CAN packets 78 due to the relatively small size of payload 92 relative to the payloads of a TCP and/or IP packet. When sending TCP and/or IP packets over an RS-485 medium 56*c* and/or an I-Squared-C medium 56*d*, multiple packets 120 may or may not need to be sent for a single IP and/or TCP packet, depending upon the payload length implemented for packets 120 and the length of the IP and/or TCP packet.

In addition to TCP and IP packets, still other types of protocols may be used to communicate over one or more of the various media 56. For example, in addition to using the protocols of messages 80 for communicating over CAN medium 56*b*, one or more nodes may also or alternatively communicate over CAN medium 56*b* using the standard CANopen communication protocol (such as specified in the CAN in Automation (CiA) 301, 401, 402, and other standards). Still further, one or more nodes 54 may be configured to communicate using CANopen over the Ethernet medium 56*a*, RS-485 medium 56*c*, and/or the I-Squared-C medium 56*d*. Still other communication protocols corresponding to layer 3 (e.g. the network layer) and above of the OSI model may be utilized for communicating over the various media 56*a-d*.

In some embodiments, packets 120 may be also or alternatively be communicated over Ethernet medium 56*a*. In such embodiments, one or more packets 120 are encapsulated within the payload 116 of an Ethernet frame 104. Alternatively, if a packet 120 is too large for a single Ethernet frame 104, the packet 120 is broken up into smaller pieces, each of which is encapsulated in an Ethernet frame.

In light of the foregoing, it can be seen that, in some embodiments, one or more nodes may communicate over a common communication medium 56 using a common data link layer protocol, but send messages over the medium 56 using the common data link layer protocol that are formatted in different manners. For example, in some embodiments, a message, such as message 80 is sent over an Ethernet connection between nodes. The nodes may also send other types of messages over the Ethernet node, such as a TCP and/or IP packet, and/or a CANOpen packet, or still another type of packet. Alternatively, TCP, IP, CANOpen, message 80, and/or other types of packets may all be sent between nodes over a common CAN data link layer. Still other types of messages and/or other data link layers may be used for sending multiple types of messages.

Figure 7:
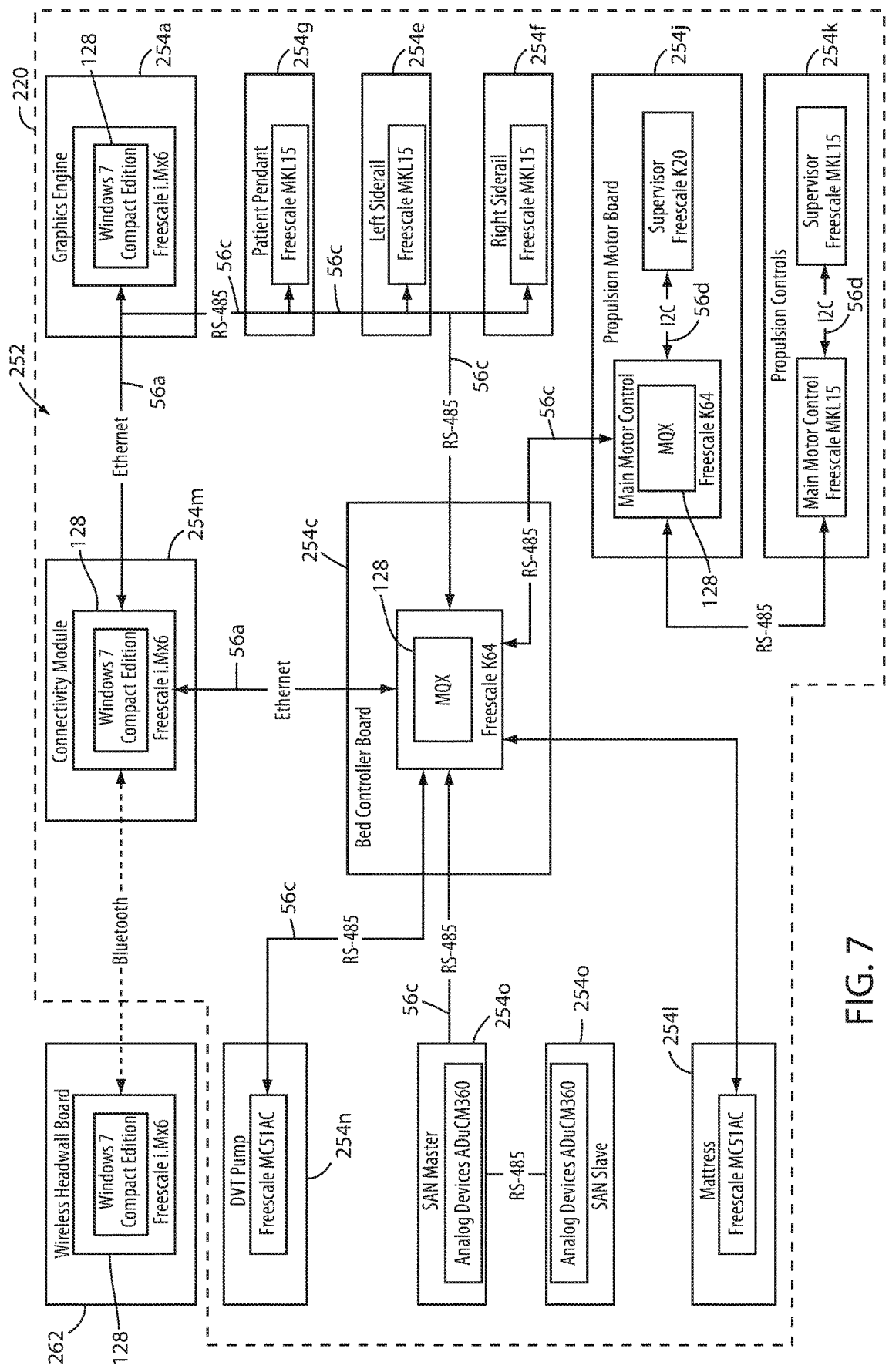
FIG. 7 is a block diagram of an alternative control system that may be incorporated into the person support apparatus of FIG. 1.

FIG. 7 illustrates an alternative control system 252 implemented in an alternative patient care device, such as, but not limited to, a person support apparatus 220. For purposes of the following description, the patient care device will be described as a person support apparatus 220, but it will be understood that person support apparatus 220 may take on other forms, as discussed above with respect to person support apparatus 20. Further, although control system 252 is shown in FIG. 7 as being implemented in person support apparatus 220, it will be understood that control system 252 can be substituted for control system 52 and incorporated into person support apparatus 20, and that control system 52 can be substituted for control system 252 and incorporated into person support apparatus 220.

As can be seen in FIG. 7, control system 252 includes a plurality of nodes 254. Those nodes 254 that perform the same or similar functions as nodes 54 are given the same number and letter references as their corresponding nodes in control system 52. For example, graphics engine node 254a of control system 252, like graphics engine node 54a of control system 52, controls the graphics that are displayed on one or more displays of person support apparatus 220. Those nodes 254 of control system 252 that do not have a functional counterpart in control system 52 are given a letter reference different from any of the letter references of nodes 54 of control system 52. For example, control system 52 does not include a dedicated mattress node, so mattress node 254*l* of control system 252 has been assigned a letter designation (1) that is not used with any of the nodes of control system 52.

Those nodes 254 of control system 252 that carry out a function similar to a counterpart node 54 of control system 52 include the following: graphics engine node 254a, left siderail node 254e, right siderail node 254f, pendant node 254g, propulsion motor control node 254j, propulsion control node 254k, and motion control node 254c. Nodes that do not have a functional counterpart in control system 52 include the following: mattress node 254*l*, a connectivity node 254m, a DVT node 254n, and a load cell node 254o. Control system 252 also communicates with a beacon node 262 that is not located on person support apparatus 220, but instead is mounted to a headwall, or other fixed location, within a healthcare facility. The operation of these nodes 254*l*-o and 262 will now be described in more detail.

Mattress node 254*l* is incorporated inside of a mattress supported on person support apparatus 220. That is, the electronics of mattress node 254*l* reside inside the mattress, such as within a control box. Such a control box includes a controller for overseeing the inflation and deflation of one or more fluid bladders within the mattress, and/or for overseeing the operation of one or more patient turning structures (such as, but not limited to, fluid bladders) within the mattress, and/or for overseeing other operations. One example of such a control box (alternatively referred to as a pump box) is disclosed in commonly assigned. U.S. patent application Ser. No. 13/836,813 filed Mar. 15, 2013, by inventors Patrick Lafleche et al. and entitled INFLATABLE MATTRESS AND CONTROL METHODS, the complete disclosure of which is hereby incorporated herein by reference. Other constructions of mattress node 254*l* are also possible. In some embodiments, the control of the mattress is carried out by a user inputting one or more commands or instructions into user interface 50. In such embodiments, the commands or instructions are forwarded by control system 252 to node 254*l*, which carries out the commands or instructions.

Connectivity node 254m, in one embodiment, combines together the functions of headwall node 54i and off-board communications node 54h of control system 52. Thus, connectively node 254m controls the communication between control system 52 and any off-board devices, including, but not limited to, location beacons, nurse call systems, WiFi access points, and other devices. DVT node 254n controls the operation of a Deep Vein Thrombosis (DVT) device that may be used to help prevent and/or treat DVT for a patient supported on person support apparatus 220.

Load cell node 254o communicates with and oversees the operation of a plurality of load cells that are integrated into person support apparatus 220 and that detect the amount of weight supported on support deck 30 of person support apparatus 20. In the embodiment shown, a first load cell node 254o communicates directly with motion control node 254c while a second load cell node 254o communicates directly only with the first load cell node 254o. Each of these nodes 254o processes the outputs from two load cells. In one embodiment, each of the load cell nodes 254o is constructed and functions in the same manners as the signal acquisition nodes described and disclosed in commonly assigned U.S. patent application Ser. No. 62/428,834 filed Dec. 1, 2016, by inventors Marko Kostic et al. and entitled PERSON SUPPORT APPARATUSES WITH LOAD CELLS, the complete disclosure of which is incorporated herein by reference.

In at least one embodiment, beacon node 262 provides the same functionality as beacon 62 and nurse call interface 64 of control system 52. Beacon node 262 therefore provides a wireless communication channel for receiving messages from person support apparatus 220 and forwarding those message to a conventional nurse call system, and vice versa. Beacon node 262 also responds to wireless interrogations from connectivity node 254m with a short-range transmission of a location identifier. The location identifier is used to determine the location of person support apparatus 220. In some embodiments, beacon node 262 may also communicate either wirelessly or by wires with a local area network of a healthcare facility.

The messages passed by beacon node 262 between person support apparatus 220 and either a conventional nurse call system and/or a local area network of a healthcare facility include the following: messages indicating that an occupant of person support apparatus 220 has exited, or is about to exit, from person support apparatus 220; messages to turn on or off one or more room lights; messages to turn on or off one or more reading lights; messages to increase or decrease the volume of a nearby television set; messages to change a channel of the nearby television set; messages containing audio packets generated from one or more microphones on the person support apparatus 220 into which an occupant of person support apparatus 220 speaks when desiring to communicate with a remote caregiver; messages indicating the current status of one or more siderails 36 of person support apparatus 220 (e.g. whether the side rails are up or down, or have changed position); messages indicating the current status of a brake on person support apparatus 220; messages indicating the current status of the height of support deck 30 relative to base 22 (e.g. such as whether support deck 30 is at its lowest height or not); messages indicating the current angle of head section 42 with respect to horizontal; messages indicating the current status of an exit detection system (e.g. whether the exit detection system is armed or not); messages indicating the current charging status of one or more batteries on person support apparatus 220; messages indicating the current status of an alternating current (A/C) power cable on person support apparatus 220 (e.g. whether it is plugged in or not); diagnostic information about person support apparatus 220; and/or any other messages containing information about person support apparatus 20 which may be useful to communicate to a remote location. Such messages originate from, or are destined to, one or more of the nodes 254 of person support apparatus 220.

The nodes 254 of control system 252 are connected together by one or more communication media 56. In the embodiment illustrated in FIG. 7, control system 252 includes Ethernet media 56a, RS-485 media 56c, and I-Squared-C media 56d. As with control system 52, the particular combination of media 56 used within control system 252 can be varied from the specific set shown in FIG. 7.

Nodes 254 of control system 252 are adapted to perform the same types of conversions between different communication protocols for transmitting messages over the various communication media 56 as the nodes 54 of control system 52 were described previously as doing. Thus, nodes 254 are capable of performing the same conversions of messages 80 between Ethernet frames 104 and packets 120 as was described above. Although control system 252 does not include any CAN communication media 56b, it will be understood that it can be modified to do so, and that when so modified, at least some of the nodes 254 can be adapted to convert messages 80 to and from CAN packets 78.

In summary, control system 252, like control system 52, includes nodes that convert one or more packets formulated according to a layer 3 (or higher) protocol (e.g. IP, TCP, FTP, a non-standard layer 3 protocol, etc.) into multiple different layer 2 (or lower) formats (e.g. Ethernet frames, CAN packets, non-standard packets, etc.). Further, one or more nodes 254 of control system 252 are adapted to convert one or more packets formulated according to a layer 2 (or higher) protocol (e.g. Ethernet frame, CAN packet, a non-standard packet) into a different layer 2 format (e.g. Ethernet frame, CAN packet, a non-standard packet). Still further, one or more nodes 254 of control system 252 are adapted to transmit a specific type of layer 2 packets (e.g. CAN packet, Ethernet frame, non-standard packet) over different physical layers (e.g. RS-485, I-squared-C, Ethernet media, etc.), as well as to transmit different types of layer 2 packets over a common physical layer. The packets contain, either wholly or partially, data that defines various messages communicated between the nodes 254. The messages include not only messages regarding the operation of the various components of person support apparatus 220, but also messages used for setting up and maintaining the communication functions between the nodes 254 (e.g. setting baud rates for RS-485 and/or I-Squared-C media; sharing addresses, transmitting heartbeat messages, notifying nodes 254 of the addition, removal, and/or malfunction of other nodes 254, etc.).

As shown in FIG. 7, control system 252 includes a plurality of nodes 254 that use different operating systems 128, as well as some nodes that do not use any operating system at all (e.g. nodes 254k, 254o, etc.). The operating systems 128 include the commercially available Windows® Embedded Compact (formerly known as Windows® Embedded CE and Windows® CE) and the commercially available Message Queue eXecutive (MQX) operating system developed by Precise Software Technologies, Inc. and sold by Freescale, among other vendors. Other operating systems 128 may be used by one or more of the nodes 254 of control system 252. Both of these operating systems 128 are hard real time operating systems (i.e. they are operating systems that can meet a deadline deterministically, as opposed to soft real time operating systems that are only capable of meeting a deadline usually or generally). In some embodiments, control system 252 is modified to include, in addition to at least one hard real time operating system 128, at least one soft real time operating systems and/or at least one non-real time operating system.

Although not described above with respect to control system 52, it will be understood that one or more of the nodes 54 of control system 52 may use an operating system 128 that is different from at least one other operating system 128 used by a node 54. Further, the operating system 128 used within control system 52 may include both real-time operating systems (hard and/or soft) and non-real-time operating systems. Still further, some of the nodes of control system 52 may be configured to not utilize any operating system at all.

Although the control systems 52 and 252 discussed herein have been described as specifically being for use in a person support apparatus (20 or 220), it will be understood that these types of control systems 52 and/or 252 may be incorporated into other patient care devices. As one example, the packet reformulation abilities and multi-media communication abilities of control systems 52 and/or 252 (as described more fully above), may be incorporated into thermal control systems used to control the temperature of a patient. One such suitable thermal control system is described in more detail in commonly assigned U.S. patent application Ser. No. 14/282,383 filed May 20, 2014, by inventors Christopher Hopper et al., and entitled THERMAL CONTROL SYSTEM, the complete disclosure of which is incorporated herein by reference. Other types of thermal control systems, as well as other types of patient care devices, may also incorporate the multi-media communication and packet reformulation functions described herein.

Various additional alterations and changes can be made to the above-described embodiments without departing from the spirit and broader aspects of the disclosure as defined in the appended claims, which are to be interpreted in accordance with the principles of patent law including the doctrine of equivalents. This disclosure is presented for illustrative purposes and should not be interpreted as an exhaustive description of all embodiments of the disclosure or to limit the scope of the claims to the specific elements illustrated or described in connection with these embodiments. For example, and without limitation, any individual element(s) of the described disclosure may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present disclosure is not limited to only those embodiments that include all of these features or that provide all of the stated benefits, except to the extent otherwise expressly set forth in the issued claims.

Any reference to claim elements in the singular, for example, using the articles "a," "an," "the" or "said," is not to be construed as limiting the element to the singular.

What is claimed is:

1. A person support apparatus comprising:
    a support surface adapted to support a person;
    first, second, and third nodes adapted to perform first, second, and third functions, respectively, associated with the person support apparatus;
    a first communication medium coupled between the first node and second node;
    a second communication medium coupled between the second node and third node; and
    a controller associated with the second node, the controller adapted to process a message received via the first communication medium and sent from the first node using a first communication protocol, convert the message from the first communication protocol to a second communication protocol, and forward the message over the second communication medium to the third node using the second communication protocol, wherein the message travels over the first communication medium as a first packet having a first payload and a first header, and the message is forwarded over the second communication medium as a second packet having a second payload and a second header.

2. The person support apparatus of claim 1 wherein the first communication protocol is an Ethernet communication protocol and the second communication protocol is a non-Ethernet protocol.

3. The person support apparatus of claim 1 wherein one of the first and second communication media conforms to the RS-485 standard of the Telecommunications Industry Association and Electronic Industries Alliance (TIA/EIA) and the other of the first and second communication media conforms to the Controller Area Network (CAN) 11898-2 standard of the International Organization for Standardization (ISO).

4. The person support apparatus of claim 1 wherein the first and second communication protocols are both selected from the following group: a Controller Area Network (CAN) protocol (ISO 11898-1), an RS-485 protocol, an I2C protocol, an Ethernet protocol (IEEE 802.3), and a Serial Peripheral Interface (SPI) protocol.

5. The person support apparatus of claim 1 wherein the controller moves at least some data contained within the first header into the second payload.

6. The person support apparatus of claim 1 wherein the controller moves at least some data contained within the first payload into the second header.

7. The person support apparatus of claim 1 wherein the controller moves the entire first header and first payload into the second payload.

8. The person support apparatus of claim 1 wherein the first payload of the first packet includes a first identifier identifying a final destination of the message and the controller is adapted to insert the first identifier into the second header of the second packet.

9. The person support apparatus of claim 1 wherein the third node is coupled to a fourth node via a third communication medium, and the third node includes a second controller adapted to process the message received via the second communication medium and sent from the second node using the second communication protocol, convert the message from the second communication protocol to a third communication protocol, and forward the message over the third communication medium using the third communication protocol.

10. The person support apparatus of claim 1 wherein:
    the controller includes a first microcontroller configured to use a first operating system;
    at least one of the first and third nodes includes a second controller configured to use a second operating system;
    one of the first and second operating systems is a real-time operating system and the other of the first and second operating systems is not a real-time operating system; and
    the real-time operating system is used to control at least one motor on the person support apparatus.

11. The person support apparatus of claim 1 wherein the first node controls a motor on the person support apparatus and the second node controls graphics displayed on a display of the person support apparatus.

12. A person support apparatus comprising:
    a support surface adapted to support a person;
    a node adapted to perform a function associated with the person support apparatus;
    a first communication medium coupled to the node;
    a second communication medium coupled to the node; and
    a controller associated with the node and adapted to reformulate a packet received in a first format via the first communication medium into a second format, the controller further adapted to forward the reformulated packet over the second communication medium, wherein the packet includes a header and a payload, the reformulated packet includes a reformulated header and a reformulated payload, the reformulated header includes at least some data from the payload of the packet, and the reformulated payload includes at least some data from the header of the packet.

13. The person support apparatus of claim 12 wherein the reformulated packet includes a first reformulated packet containing a first portion of a payload of the packet and a second reformulated packet containing a second portion of the payload of the packet, the controller adapted to transmit both the first and second reformulated packets over the second communication medium.

14. A person support apparatus comprising:
    a support surface adapted to support a person;
    a first node adapted to perform a first function associated with the person support apparatus;
    a second node adapted to perform a second function associated with the person support apparatus
    a communication medium coupled between the first node and the second node; and
    a controller associated with the first node, the controller adapted to send a first message and a second message over the communication medium to the second node using a first data link layer protocol, wherein the first message is defined according to a first message protocol and the second message is defined according to a second message protocol, wherein the first data link layer protocol defines a packet structure having a header and a payload, and the controller is adapted to insert the entire first message into the payload of a first packet and to insert only a portion of the second message into the payload of a second packet.

15. The person support apparatus of claim 14 wherein the first message protocol is a publicly available protocol and the second message protocol is a confidential proprietary protocol.

16. The person support apparatus of claim 14 wherein the first data link layer protocol is defined in accordance with the Controller Area Network (CAN) 11898-1 standard of the Organization for Standardization (ISO).

17. The person support apparatus of claim 14 wherein the first data link layer protocol is defined in accordance with at least one of the 802.3 standards of the Institute of Electrical and Electronics Engineers (IEEE).

18. The person support apparatus of claim 14 wherein the first message protocol is an Internet Protocol (IP).

19. The person support apparatus of claim 14 wherein the first message protocol is defined in accordance with specification 301 of the CAN in Automation (CiA) organization.

20. The person support apparatus of claim 14 further comprising:
   a plurality of lifts adapted to change a height of the support surface;
   a plurality of siderails movable between raised and lowered positions; and
   a plurality of wheels adapted to support the person support apparatus.

21. The person support apparatus of claim 14 further comprising a second controller associated with the second node, wherein the controller adapted to execute a first operating system and the second controller is adapted to execute a second operating system.

\* \* \* \* \*